US010273522B2

(12) United States Patent
Sengupta et al.

(10) Patent No.: US 10,273,522 B2
(45) Date of Patent: *Apr. 30, 2019

(54) RAPID DETECTION OF VIABLE BACTERIA SYSTEM AND METHOD

(71) Applicant: The Curators of the University of Missouri, Columbia, MO (US)

(72) Inventors: Shramik Sengupta, Columbia, MO (US); Sachidevi Puttaswamy, Columbia, MO (US); Hsueh-Chia Chang, Granger, IN (US)

(73) Assignees: The Curators of the University of Missouri, Columbia, MO (US); University of Notre Dame de Lac, Notre Dame, IN (US)

( * ) Notice: Subject to any disclaimer, the term of this patent is extended or adjusted under 35 U.S.C. 154(b) by 1416 days.

This patent is subject to a terminal disclaimer.

(21) Appl. No.: 14/099,110

(22) Filed: Dec. 6, 2013

(65) Prior Publication Data

US 2014/0162310 A1 Jun. 12, 2014

Related U.S. Application Data

(63) Continuation of application No. 12/896,188, filed on Oct. 1, 2010, now Pat. No. 8,635,028.

(60) Provisional application No. 61/278,156, filed on Oct. 2, 2009.

(51) Int. Cl.
| | |
|---|---|
| *G01N 33/50* | (2006.01) |
| *C12Q 1/06* | (2006.01) |
| *C12Q 1/04* | (2006.01) |
| *G01N 33/543* | (2006.01) |
| *B01L 3/00* | (2006.01) |

(52) U.S. Cl.
CPC ............... *C12Q 1/06* (2013.01); *C12Q 1/04* (2013.01); *G01N 33/5438* (2013.01); *B01L 3/502715* (2013.01)

(58) Field of Classification Search
None
See application file for complete search history.

(56) References Cited

U.S. PATENT DOCUMENTS

| | | | |
|---|---|---|---|
| 7,465,560 B2 | 12/2008 | Hirleman, Jr. et al. | |
| 2004/0197899 A1* | 10/2004 | Gomez | G01N 33/5438 435/287.2 |
| 2007/0212257 A1 | 9/2007 | Nolte et al. | |
| 2010/0120016 A1 | 5/2010 | Li et al. | |

FOREIGN PATENT DOCUMENTS

WO  WO/2009/136157  *  7/2009  ........... G01N 33/487

OTHER PUBLICATIONS

Sengupta et al. Lab Chip, 2006, 6, 682-692 (Year: 2006).*
Yang et al. Biotechnology Advances, 2008, p. 135-150 (Year: 2008).*
U.S. Appl. No. 12/896,188 Office Action dated Nov. 16, 2012 (15 pages).
U.S. Appl. No. 12/896,188 Office Action dated Aug. 17, 2012; (8 pages).
U.S. Appl. No. 12/896,188 Office Action dated Mar. 20, 2013; (13 pages).

* cited by examiner

*Primary Examiner* — Michael L Borin
(74) *Attorney, Agent, or Firm* — Polsinelli PC

(57) ABSTRACT

An improved system and method is provided for detecting viable bacteria in a suspension sample. A sample of a suspension in which bacterial presence is suspected is collected from a source and a portion of the sample transferred to a microfluidic unit. A series of analysis signals at different frequencies are applied to the sample portion. An impedance is measured via a signal analyzer for the sample portion for each of the analysis signals to define an impedance data set. An initial bulk capacitance value is determined for a model circuit based on the impedance dataset. After a predetermined time period, a new bulk capacitance value is determined for on another portion of the sample. The difference between the new bulk capacitance and the initial bulk capacitance value is compared to a threshold value to determine if viable bacterial is present in the sample.

18 Claims, 23 Drawing Sheets

RAPID DETECTION OF VIABLE BACTERIA SYSTEM AND METHOD

RELATED APPLICATIONS

This application is a continuation of U.S. patent application Ser. No. 12/896,188, filed Oct. 1, 2010, entitled Rapid Detection Method For Viable Bacteria, which claims priority to U.S. Patent Application No. 61/278,156, filed Oct. 2, 2009, and entitled Rapid Detection Method For Viable Bacteria, the entire contents of which are incorporated herein by reference.

GRANT STATEMENT

None.

FIELD

The present invention relates to a system and method for detecting the presence of viable bacteria in suspensions. More specifically, the invention relates to a system and method for detecting viable bacteria in a suspension based on changes in impedance induced by the proliferation of bacteria in the suspension.

BACKGROUND

The process of pasteurization involves heating liquid food products like milk, juices, etc to kill harmful organisms such as viruses, bacteria, molds, and yeast. However, some amount bacteria may survive the pasteurization process or may be inadvertently introduced during further processing. Such bacteria typically cause spoilage of food products and has been estimated to cause economic losses of $1 billion each year. Moreover, if the surviving bacteria are pathogenic, outbreaks of food borne illnesses may occur among consumers who assumed that the food product was risk-free since it had been pasteurized. In the United States alone, it has been estimated that approximately 76 million food borne illnesses occur per year. It has also been estimated that such illnesses result in up to 5000 deaths and have an adverse economic impact of $6.5-$34.9 billion each year.

Detecting and quantifying bacteria that survive treatments such as pasteurization is an important step in assuring food quality and food safety and in complying with standards set by appropriate governing bodies or trade organizations. For instance, the United States Pasteurized Milk Ordinance requires "Grade A" pasteurized milk to have a total bacterial count of ≤20,000 colony forming unit (CFU)/ml and a coliform count of ≤10 CFU/ml. As a consequence, those who produce and/or market food products have to perform microbiological tests to satisfy themselves, and the governing bodies, regarding the efficacy of their processes designed to keep the numbers of bacteria within the stipulated range. It is important to their economic operation that they do so with the least possible expenditure of resources (material and labor).

There are presently several ways to detect bacteria in liquid samples like milk and juice. They can be broadly classified into three broad classes: (a) traditional methods such as plate cultures and biochemical assays, (b) DNA and antibody based methods, often involving micro/nano particles and fluorescence, (c) other "automated" techniques that rely on monitoring the effects of bacterial metabolism on the medium. Of these, traditional methods are the most extensively used, and often serve as the standard to which other techniques are compared. However, such traditional methods are tedious, labor intensive, and require very long times to detect bacteria, which can range from overnight to weeks depending on the type of the organism and medium used.

DNA and antibody based methods overcome many of the disadvantages of the traditional methods. They are rapid, require less reagents and labor, and are able to identify the species/strain of the bacteria present relatively easily. However, DNA and antibody based methods cannot distinguish between viable and dead bacteria, and hence their applicability in many situations (such as that described earlier) is limited.

The commercially available automated methods include devices such as the Bactec™ that detects the amount of radio-labeled carbon dioxide released, Coli-Check™ swabs that use Bromocresol Purple as an indicator to measure the decrease in pH due to bacterial metabolism, and the Bactometer™ (Bactomatic Ltd.), Malthus 2000™ (Malthus Instruments Ltd.) and RABIT™ (Don Whitley Scientific Ltd.) systems, that use electrical impedance. A summary of various automated methods already commercialized, and the times to detection ("TTD") for these methods (for various mentioned initial loads) are given in Table 1.

TABLE 1

Summary of Existing Automated Methods

| Commercial name | Method employed | Initial load | Microorganisms | TTD |
| --- | --- | --- | --- | --- |
| RABIT (Don Whitley Scientific Ltd., Shipley, UK) | Change in solution conductance | 1 CFU/ml | coliforms | 16.1 hrs |
| Bactometer (Bio Merieux, Nuertingen, Germany) | Impedance microbiology | >$10^5$ CFU/ml | Mainly E. coli | 4 hours |
| Malthus systems (Malthus Instruments Ltd., Crawley, UK) | Conductance change of the fluid | 100 CFU/ml | C. Sporogenes | 15.5 hrs |
| BacTrac (Sylab) | Impedance analyzer | 100 CFU/ml | P. Aeruginosa | 30 hours |

The common underlying feature of these techniques, including those which use electrical impedance, is based on bacterial metabolism to produce a discernable change in a material property of the medium (such as pH, optical density, amount of carbon dioxide dissolved, electrical conductivity). The amount of metabolite processed by an individual bacterium is extremely small. Hence, there has to be a sufficiently large number of bacteria present (either a priori or arising due to proliferation from the smaller number initially present) before the signal generated (change in the material property of the suspension) can be effectively measured. If the bacterial count in the original suspension happens to be small (1000 CFU/ml or lower), one must wait for cells to proliferate to an appropriately high number (often ~$10^6$ CFU/ml or greater) before a discernable change in the physical properties of the medium (such as pH, $O_2/CO_2$ concentration, conductivity etc) can be noticed. Thus, for low initial loads, current commercial automated systems take almost as long as the plate-cultures (overnight or longer) to provide the desired result.

Recently, there have been efforts to increase the ease of handling, cut costs, and most importantly, reduce TTDs by using microfluidic systems to miniaturize the automated methods. For example, chip-based micro-devices have been developed in which the pH and impedance of a sample contained therein are monitored in order to detect bacterial metabolism, and various additional modifications like the use of interdigitated microelectrodes, and arrays of microelectrode based biosensors have been tried in order to increase the sensitivity of measurements (with respect to conventional electrodes), and thus further decrease the TTD. While these efforts were successful in the sense that their TTDs are lower than those of the commercially available devices, they continue to be limited by the amount of time it takes for bacterial metabolism to significantly alter the composition of the medium when bacterial loads are low. One method previously attempted to overcome this drawback involved concentrating the bacterial cells from dilute samples to a small volume by using dielectrophoresis (DEP) prior to culture, and then detecting changes in medium composition as before. While the culture time needed for detection was reduced, one needs to take into account the time needed for concentration using DEP (an additional 2-3 hours) as well to get effective TTDs. Again, while successful, the actual method of detection still relies on bacterial metabolism, with its inherent limitations (as discussed earlier).

Therefore, there is a need to provide a new and improved method to detect viable bacteria in a suspension based on the changes of capacitance of the suspension due to the bacteria proliferation. There is another need to provide a new system to detect viable bacteria in a suspension based on the changes of capacitance of the testing suspension.

SUMMARY

The invention provides a new and improved method to detect viable bacteria and its proliferation in a suspension based on the changes in the capacitance of material in the interior bulk of the suspension. According to one embodiment of the invention, the detection method includes the steps of 1) incubating a suspension containing viable bacteria 2) obtaining impedance measurements at multiple pre-determined frequency to obtain a parameter (using a novel theoretical electronic circuit model) that reflects the amount of charge stored in the interior bulk of the suspension and repeating this after pre-determined intervals of time and 3) analysing changes in the value of the obtained parameter with time to infer the presence, or lack thereof, of viable bacteria in the suspension.

The invention also provide a detection system to accomplish the inventive method. The detection system composed of 1) a microfluidic channel with defined geometric properties having electrodes on its two ends, wherein a testing suspension may be injected into the channel, 2) an impedance mesuring device to obtain impedances of the testing suspension at multiple frequencies and different time intervals, and 3) a data analysis means to analyzing the impedances and obtaining the parameter of the interest based on the related circuit model.

DETAILED DESCRIPTION OF INVENTION

Figure 1A:
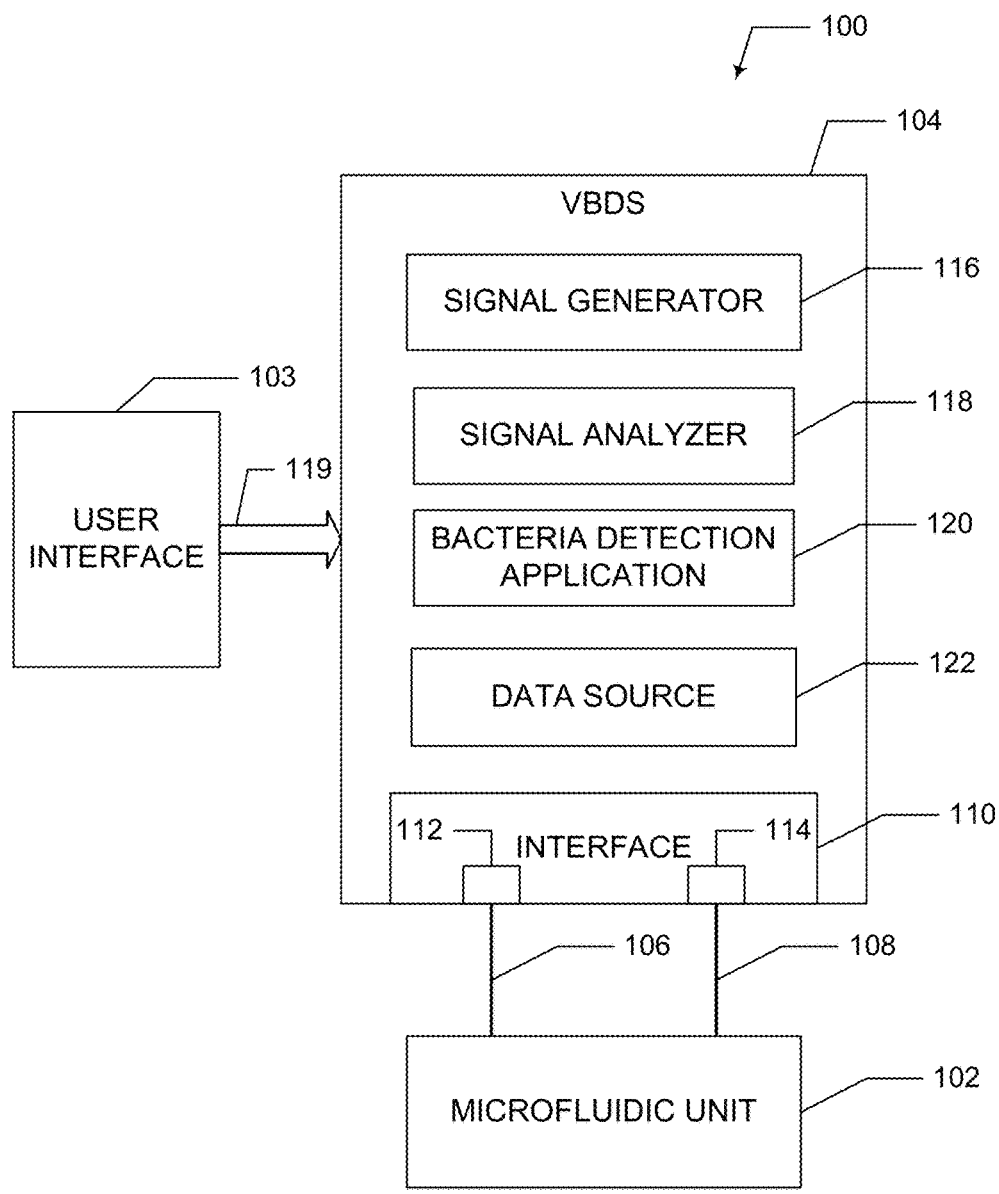
FIG. 1A is a block diagram of an emplary computing environment for implementing a viable bacteria detection system.

The present invention provides a new and improved method for detecting viable bacteria in suspensions, such as fluid food products, blood samples, and environmental water samples, and other liquid media samples. Unlike the existing metablism based methods used to detect bacteria, the inventive method is based on the ability of viable bacteria to store electric charge. As the number of viable bacteria in a suspension increases due to the reproduction of the previously existing viable bacteria, the charge carrying capacity of the particular suspension as a whole (its bulk capacitance) increases. The inventive method is designed to magnify the effect at measureable frequencies (<100 MHz) and apply the inventive data analysis to filter out other effects such as change in temperature that can affect measured impedance values. Employing the inventive methods, the bacterial proliferation in liquid media may be detected much faster (about 4 to 10 times) than existing methods.

The present invention also provides a new and improved system for rapid detection of bacterial proliferation in suspensions. The inventive system includes 1) a microfluidic testing channel unit with electrodes at its opposite ends, whereas a testing suspension may be injected into the testing channel at a pre-determined amount and interval, 2) an impedance detecting means to measure the impedances of the testing suspension at a series of pre-determined frequencies ranging from about 10 KHz to about 100 MHz, whereas the impedance detecting means is in electrical communication with the electrodes, and 3) a data analysis means that processes the impedances.

The present inventive method and system may be employed in various applications. For example, the inventive method may be applied in food quality testing. Producers of bottled products like pasteurized milk, juice, etc. as well as operations like meat processing factories need to ensure that the procedures they adopt are effective to eliminate harmful bacteria from their products. That is, producers need to verify that processes, such as pasteurization, irradiation, etc. are effective to eleiminate viable bacteria left in the product or that the amount of viable is below a certain threshold. Plating techniques, or some of the "automated" technique, such as RABIT, are examples of techniques that are currently used to detect viable bacterial. The inventive method can perform much better than the current automated methods.

The inventive method and system may be employed in the rapid detection of slow glowing pathogens like *mycobacteria* for animal and human health applications. *Mycobacteria* are a class of bacteria that are responsible for a number of important diseases both in animals and humans. For example, such *mycobacteria* can cause Johne's Disease in cattle, which is estimated to cost the U.S. cattle industry over $2 Billion a year. As another example, similar *mycobacteria* can cause Tuberculosis in humans. *Mycobacteria* are characterized by a uniquely thick cell wall and slow metabolism that enable to survive many conditions that kill almost all other bacteria. Their unique physiology makes detecting them in samples such as sputum and fecal extracts an extremely time consuming process. Typically, the biological sample is first subjected to conditions that kill other microorganisms—and then it is cultured (mycobacteria are allowed to grow and proliferate). Automated techniques such as the TREK-VET system relies on a decrease in the concentration of dissolved oxygen to detect viable *Mycobacterium avium* ssp. Paratuberculosis, which is the causative organism for Johne's Disease. Another automated technique, such as BACTEC system, uses the detection of radioactive $CO_2$ released from radiaactive solid nutrients to detect the presence of viable *M tuberculosis*. Both of these systems can typically take weeks (e.g., 40 days) to provide results. Estimately, the inventive method and system can cut down the time to detection by a factor of 4 to 10.

Additionaly, the inventive method and system may be employed to assist blood culture analyses. For example, septicemia or sepsis is the infection of pathogenic microroganisms into the bloodstream. There are over 200,000 cases of sepsis in the United States each year. Typically, when a patient begins to demonstrate clinical sysmptoms of the disease, pathogens are present at less than 10 cfu/ml of blood. To detect these pathogens, about 3-10 ml of blood is cultured (incubated at 35° C. under aerobic/anaerobic conditions) for 2 to 7 days. Estimately, the inventive method/system may bring the TTD of this procedure down by a similar factor. Since the rapid diagnosis of sepsis enables the clinician to commence proper treatment quickly, which will make a significant impact in reducing the fatality rate associated with sepsis (which is currently close to 30%).

Furthermore, the inventive method/system may be applied in environmental water quality testings. Currently it takes more than 2 days to ascertain presence, or lack thereof, of viable pathogens (such as coliforms) after reports of supected infections in areas such as recreational water bodies (E.g. beaches, lakeshores etc). The inventive method/system may cut down the TTDs for these cases as well.

Example of Bacterial Proliforation Testings

The present invention also provides several examples of bacterial proliforation testings using the inventive method/system.

Sample preparation and inoculation of bacteria into samples: *Escherichia coli* K12 (ATCC 23716), and *Lactobacillus acidophilus* (Nature's Life™ Apple-honey *Lactobacillus acidophilus* probiotic) were used in this study. In order to obtain load cultures, *E. coli* K12 was incubated overnight at 37° C. in Tryptic Soy Broth (TSB) (Bacto™, BD), *Lactobacillus acidophilus* was incubated at 30° C. for about 48 hrs in MRS Broth (Difco™, BD). These were then used, in appropriate dilutions, to seed the samples in which bacterial proliferation was monitored using the inventive method. These samples included those of TSB loaded with *E. coli* (to compare the present technique to previous work), and two representative liquids to study the ability of the method to detect bacteria in food samples, [2% reduced fat milk (Prairie Farms™) for *E. coli* and preservative free apple juice (Florida's Natural™) for *Lactobacillus acidophilus*].

To facilitate growth of lactobacilli in the apple juice, its pH was adjusted to about 6 by adding potassium hydroxide (about 1 ml of 10M KOH to 50 ml of Apple Juice). The media and the food samples were all autoclaved at 121° C., 15 psi to ensure no presence of live bacteria in them. This ensures the right concentration of the bacteria in the sample when it is artificially inoculated it a bacteria of interest. The samples are allowed to cool down to room temperature before bacterial inoculation. The bacterial suspension after being incubated for specified time periods was initially assumed to contain approximately $10^9$ CFU/ml bacteria. 1 ml of *E. coli* K12 and 1 ml of *Lactobacillus acidophilus* were taken in separate eppendorf tubes and centrifuged for 8 minutes to settle the bacteria down as pellet. Then the supernatant was discarded and pellets were re-suspended in equal volume of food samples in which they were to be detected. Then the suspension was serially diluted and inoculated into the liquid samples to have different initial concentration of bacteria in them and also simultaneously the samples were plated onto petriplates to get the actual initial concentration of the inoculated bacteria in the sample.

Experimental Design: 4 sets of 9 ml of each of the liquid samples (TSB, milk or apple juice) were taken in the incubating tubes. Each tube was inoculated with the bacteria to be detected such that the final concentrations of the bacteria in the tubes were approximately 1, 10, 100 and 1000 CFU/ml respectively. The tubes were then allowed to incubate for a time period of 8 hours for 1, 10, 100 CFU/ml concentrations and 5 hours for 1000 CFU/ml concentration. At regular time intervals (30 min for 1000 CFU/ml and 1 hour for 1, 10, 100 CFU/ml) small volume (~250 µl) of the sample was taken out, injected into the cassettes and impedance measurements were made using the Agilent 4294A impedance analyzer (Agilent technologies, CA, USA) over the frequency range of 1 kHz to 100 MHz. Simultaneously at every time interval, 100 µl of the sample was taken, diluted appropriately and plated onto petri-dishes to give actual concentration of bacteria at that hour in the sample. The entire process was repeated independently at least 3 times for each targeted initial load of the system (1, 10, 100 or 1000 CFU/ml) and for all liquids (TSB, milk and apple juice).

The microfluidic cassettes used for the measurement was fabricated using liquid phase photo-polymerization of a commercially available UV curable polymer (Loctite 363™), a process that has been described elsewhere in detail. The cassettes were sterilized in an autoclave at 121° C. before use. After each of the experiment, the electrical connectors were replaced; cassettes were washed thoroughly with soap, bleach, alcohol and water, and then autoclaved.

Viable Bacteria Detection System

FIG. 1A is a block diagram of an exemplary computing environment 100 for detecting the presence of viable bacteria in a fluid sample. The computing environment 100 includes a microfluidic unit 102, an input device, 103, and a viable bacteria detection system (VBDS) 104.

According to one aspect, the microfluidic unit 102 receives a portion of a particular suspension sample from a sample collection device (not shown), such as a vial, vacutainer, or other fluid sample container. For example, the sample collection device may be a fingerstick collection device or a vacutainer that is used to collect 50-200 µl of a whole blood sample from a finger stick and to subsequently transfer at least a portion of the sample to the microfluidic unit 102. According to one aspect, the microfluidic unit 102 is a disposable closed containment device that contains reagents, fluidic channels, and biosensors. The microfluidic unit 102 also includes electrodes 106, 108 that allow input and/or output of electrical voltage and/or electrical current signals, and may simultaneously serve as a measurement electrode according to an aspect of the invention.

Figure 2A:
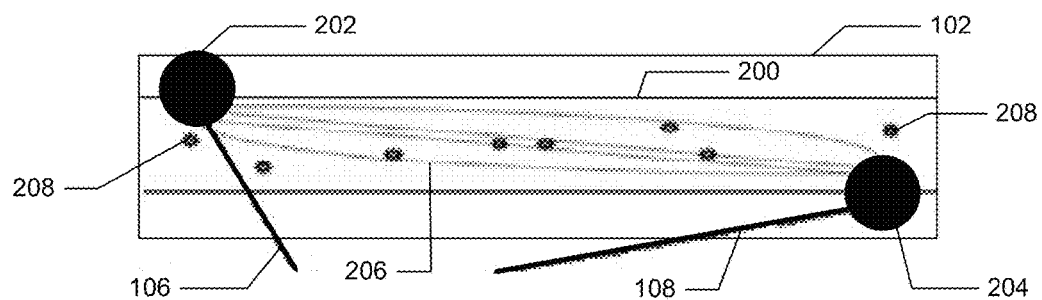
FIG. 2A depicts of a microfluidic unit with electrodes on either end loaded with suspension harboring bacteria.

Referring briefly to FIG. 2A, a schematic representation of a micro-channel 200 of the microfluidic unit 102 with electrode terminals 202, 204 on either end loaded with a suspension 206 harboring bacteria 208 is depicted. When the microfluidic unit 102 is loaded with a portion of a particular suspension 206 being investigated, the suspension 206 fills the micro-channel 200 and contacts the terminals 202, 204 of the electrical electrodes 106, 108.

Referring back to FIG. 1A, the VBDS 104 includes an interface 110 that enables the microfluidic unit 102 to be connected and disconnected to the VBDS 104. The interface 110 comprises, for example, receptacles 112, 114 for receiving electrodes 106, 108 of the microfluidic unit 102 such that the VBDS 104 can supply analysis signals to the sample and receive measurement signals from the sample. According to one aspect, the VBDS 104 comprises a signal generator 116 to generate voltage and/or current signals at various frequencies and amplitudes to apply to the electrodes the 106, 108 of microfluidic unit 102.

The VBDS 104 also includes a signal analyzer 118 to measure parameters of a circuit created by the electrical interaction between the electrodes 106, 108 and the fluid sample. According to one aspect, the signal analyzer 118 is, for example, an Agilent 4294A Impedance Analyzer that measures the electrical impedance between the electrodes 106, 108 at multiple frequencies (e.g., >500 different frequencies) between 1 KHz to 100 MHz. The signal analyzer 118 measures the magnitude and phase of an AC current that flows through the suspension upon the application of a sinusoidal AC voltage of 500 mV (peak-to-peak) and then calculates the impedance (i.e., resistance and reactance) from the measurements. Since the current is not in-phase with the applied sinusoidal voltage, the impedance, which can be considered as the AC analog of the DC resistance, has both an in-phase component called the resistance (R), and an out-of-phase component called the reactance (X) Impedance is typically represented as a complex number and as shown in equation 1

$$Z=R+jX \quad (1)$$

where $j=\sqrt{-1}$

Alternatively, the impedance can also be represented completely by its magnitude (|Z|) and its phase angle θ. The magnitude and phase angle, respectively, of the impedance, are related to the resistance and reactance by the equations.

$$Z=\sqrt{(R^2+X^2)} \quad (2a)$$

$$\theta=\mathrm{Tan}^{-1}(X/R) \quad (2b)$$

The signal analyzer 118 measures impedance by measuring the resistance (R) and reactance (X) for each sample, over the frequency range of 1 kHz to 100 MHz and hence generates an impedance data set containing the values of R and X for each of the multiple frequencies.

By obtaining impedance measurements at multiple pre-determined frequencies, a the value of the parameter in the theoretical circuit model, which reflects the amount of capacitive charge stored in the interior bulk of the suspension, can be calculated. As discussed above, the presence of bacteria in a suspension can be detected based on the changes in the bulk capacitance of the suspension over time. Thus, by repeating the process of obtaining impedance measurements at multiple pre-determined frequency after pre-determined intervals of time, the presence, or lack thereof, of viable bacteria in the suspension can be determined.

According to one aspect, the user interface 103 is a computer or processing device, such as a personal computer, a server computer, or a mobile processing device. The input device may include a display (not shown) such as a computer monitor, for viewing data, and an input device (not shown), such as a keyboard or a pointing device (e.g., a mouse, trackball, pen, touch pad, or other device), for entering data. The user interface 103 is used by a user to enter information about a particular sample to be analyzed by the VBDS 104. For example, the user uses the keyboard to interact with an entry form (not shown) on the display to enter sample information data that includes, for example, fluid type, fluid collection date and time, fluid source, etc.

The user interface device 103 can also be used by the user to generate an analysis request 119 for a particular sample to be analyzed by the VBDS 104. For example, after a portion of the particular sample in a collection device has been transferred to the microfluidic unit 102 and the microfluidic unit 102 is connected to the VBDS 104, the user interacts with an entry form (not shown) on the display of the user interface 103 to select, for example, start analysis control to generate the analysis request 119. The user interface 103 provides the analysis request 119 to the VBDS 104. The VBDS 104 initiates the operation of the signal generator 116 and the signal analyzer 118 in response to the received analysis request 119.

Subsequently, the user interface device 103 can also be used by the user to generate another analysis request 119 for another portion of the same particular sample. For example, after a pre-determined time interval expires, the user interface device 103 notifies or alerts the user to transfer another portion of the particular sample from the collection device to the microfluidic unit 102 for analysis. The microfluidic unit 102 is again connected to the VBDS 104 and the user again interacts with the entry form (not shown) on the display of the user interface 102 to select the start analysis control to generate another analysis request 119. As described in more detail below, the pre-determined time interval is a function of expected TTDs data for individual samples.

According to another aspect, the user interface device 103 can also be used by the user to define pre-determined time intervals for collecting different portions of the sample. For example, the user may define pre-determined time intervals, such as 15 minutes, 30 minutes, 1-hour, etc.

According to another aspect, the user interface device 103 can also be used by the user to define a maximum processing time for attempting to identify viable bacteria in a particular sample. For example, the user may define the maximum processing as equal to 8 hours, 24 hours, 48 hours, etc. As explained below, if the VBDS 104 does not determine that the sample has viable bacteria within the maximum processing time, the sample is deemed not to contain bacteria and the detection process is terminated.

The VBDS 104 executes a bacteria detection application (BDA) 120 to detect whether viable bacteria is present in the sample based on a change in impedance measurements of the sample over a period of time. According to one aspect, the BDA 120 determines parametric values of a model circuit based on the impedance measurements. The BDA 120 then determines whether one or more of the parametric values, such as bulk capacitance, change more than a threshold amount over the pre-determined time period. If the change in one or more of the parametric values is more than the threshold amount, then the sample is deemed to contain viable bacteria. If the amount of change in the one or more of the parametric values does not exceed the threshold amount, then the sample is not deemed to contain viable bacterial. The BDA 120 then displays whether the result of the analysis is positive or negative for viable bacteria.

The data source 122 is, for example, a computer system, a database, or another data system that stores data, electronic documents, records, other documents, and/or other data. The data source 1506 may include memory and one or more processors or processing systems to receive, process, and transmit communications and store and retrieve data. The BDA 120 retrieves the pre-determined interval data from the data source 122 to determine when to notify the user to collect another portion of the sample for analysis. According to one aspect, the data source 122 includes a sample database 124 that stores pre-determined time interval data for various fluid samples. The sample database 124 may also store impedance data or the various parametric values of the model circuit determined at different point in time for each of the various samples.

Although, the data source 122 is illustrated in FIG. 1A as being integrated with the VBDS 104, it is contemplated that in other aspects the data source 122 may be separate and/or remote from the VBDS 104. According to one such aspect, the VBDS 104 communicates with the data source 122 over a communication network, such as the Internet, an intranet, an Ethernet network, a wireline network, a wireless network, and/or another communication network, to identify relevant images, electronic documents, records, other documents, and/or other data to retrieve from the data source 122. In another aspect, the VBDS 104 communicates with the data source 122 through a direct connection.

Figure 1B:
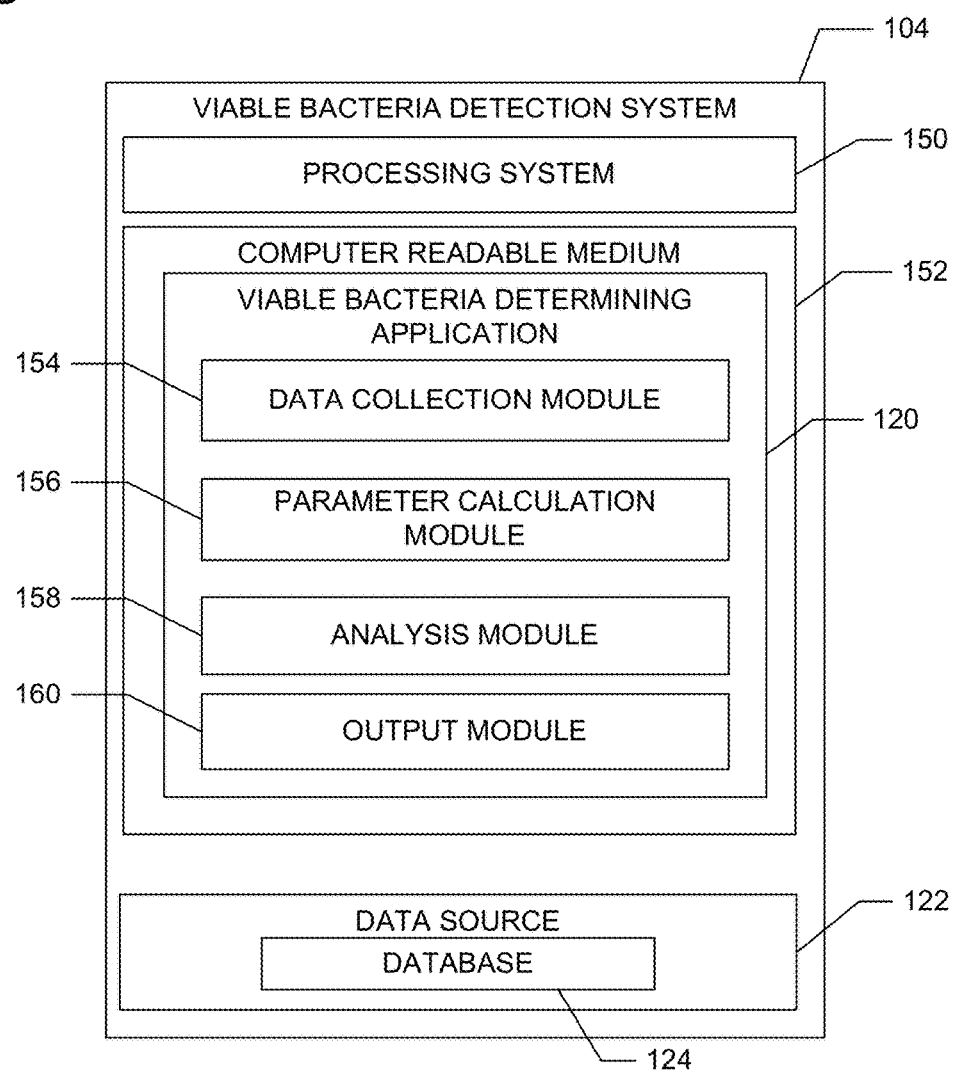
FIG. 1B is a block diagram that depicts an exemplary viable bacteria detection system.

FIG. 1B is a block diagram that depicts an exemplary BDA 120. According to one aspect, the VBDS 104 includes a processing system 150 that executes the BDA 120 to detect whether viable bacteria is in the sample based on a change in impedance measurements detected at the signal analyzer 118 over a period time. The processing system 150 includes one or more processors, and the processing system 150 can reside on a computer or other processing system.

The BDA 120 includes instructions or modules that are executable by the processing system 150 to manage the retrieval of pre-determined time interval data from the data source 122 and to detect whether there is viable bacterial in the sample changes in on or more of the determined parametric values of a model circuit. The VBDS 104 includes computer readable media 152 configured with the BDA 1512.

Computer readable medium (CRM) 152 may include volatile media, nonvolatile media, removable media, non-removable media, and/or another available medium that can be accessed by the VBDS 104. By way of example and not limitation, computer readable medium 152 comprises computer storage media and communication media. Computer storage media includes memory, volatile media, nonvolatile media, removable media, and/or non-removable media implemented in a method or technology for storage of information, such as computer readable instructions, data structures, program modules, or other data. Communication media may embody computer readable instructions, data structures, program modules, or other data and include an information delivery media or system.

A data collection module 154 activates the signal generator 116 to generate a series of analysis signals to apply to the sample at various frequencies in response to an analysis request 119 received from the user interface 103. The data collection module 154 also activates the signal analyzer 118 to obtain impedance measurement data of the sample based on the applied analysis signals in response to the received analysis request 119. The net measured impedance ($Z_{measured}$) is, as shown by equation 1 is affected by not only by the presence of conductive and capacitive (charge-storing) elements in the bulk, but also by such elements present at the electrode-solution interface. As described above, the signal analyzer 118 measures impedance by measuring the resistance (R) and reactance (X) for each sample, over the frequency range of 1 kHz to 100 MHz and hence generates the data set containing the values of R and X at each of the multiple frequencies.

A parameter calculation module 156 calculates parametric values of a model circuit based on the impedance measurement data sets received from the data calculation module 154. Each impedance data set corresponds to a series of impedance measurements obtained at various frequencies at during a particular measurement cycle. Each measurement cycle is separated by a pre-determined time interval. According to one aspect, parameter calculation module 156 employs, for example, commercial circuit analysis software (Z view) to fit the values of resistance (R) and reactance (X) for a particular impedance measurement data set to an equivalent circuit model. The parameter calculation module 156 uses the circuit model and the impedance measurement data set to estimate each of the individual parameters ($R_e$, $C_e$, $R_b$ and $C_b$) of the circuit.

Figure 2B:
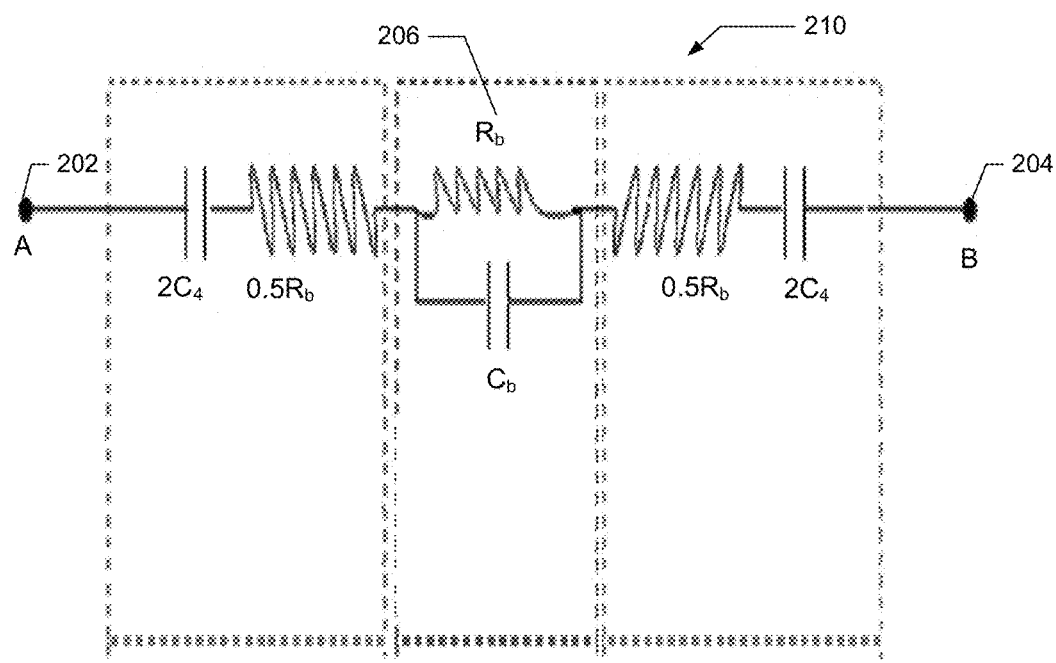
FIG. 2B is an exemplary model circuit representation of the impedance components of a microfluidic unit harboring bacteria.

Referring briefly to FIG. 2B, an example of the circuit model 210 that works well for estimating individual impedance parameters ($R_e$, $C_e$, $R_b$ and $C_b$) at low frequencies. However, the model circuit depicted in FIG. 2B may be not sufficiently accurate at estimating the parameters at higher frequencies.

Figure 3A:
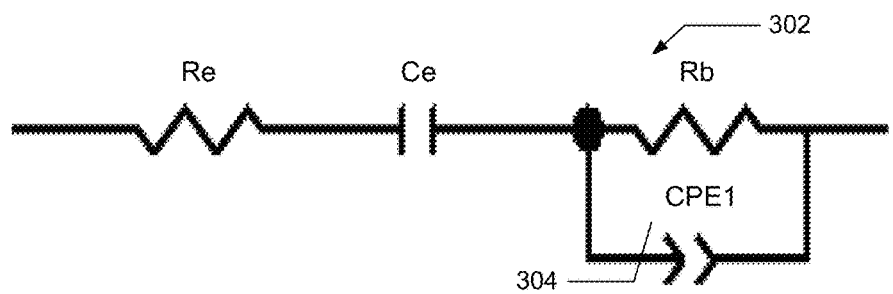
FIG. 3A shows another exemplary equivalent representation of the impedance components of a microfluidic unit harboring bacteria.

FIG. 3A depicts another circuit model 302 for estimating impedance parameters. In this model circuit 302, the bulk capacitance ($C_b$) is replaced with a Constant Phase Element (CPE) 304 and the model circuit provides a much better fit to the data obtained, as shown in the FIG. 3B-3D. The CPE 304 a non-intuitive circuit element that replaces a capacitor in a circuit when the there is some type of non-homogeneity in the system, delaying or impeding the movement of charge carriers. In more mathematical terms, the impedance of a CPE 304 is given by the equation $$Z = 0 - j(1/(wQ)^n) \quad (3)$$

As shown in equation 3, the impedance of the CPE 304 is defined by two values: the magnitude component CPE-T (Q) that is measured in farads and the phase component CPE-P (n). If CPE-P (n) equals 1 then the equation is identical to that of a capacitor. While bacteria can store a charge, it likely does not behave like ideal capacitors. Thus, using a CPE 304 to compensate for the non ideal charge storage capability of the bacterial is appropriate. The CPE is used for the data analysis, as the arc of the Cole Plot for the impedance data was a depressed semicircle or an arc of the circle rather than a perfect semicircle as would be the case if the bacteria behaved like ideal capacitors. The value of the CPE-P (n) is not a constant but is different for different samples.

Figure 3B:
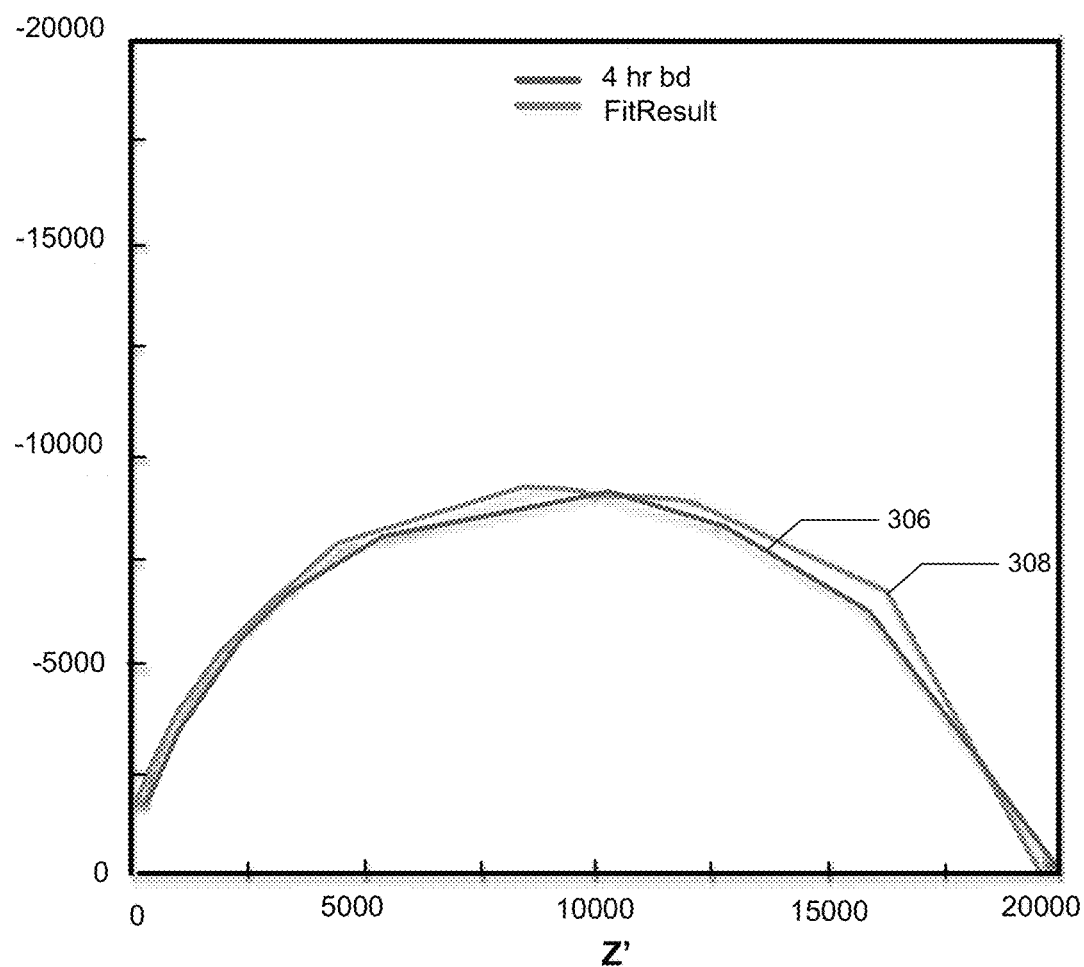
FIG. 3B is a Cole Plot of Resistance (Z') on the x-axis against Reactance (Z") on the y-axis.
Figure 3C:
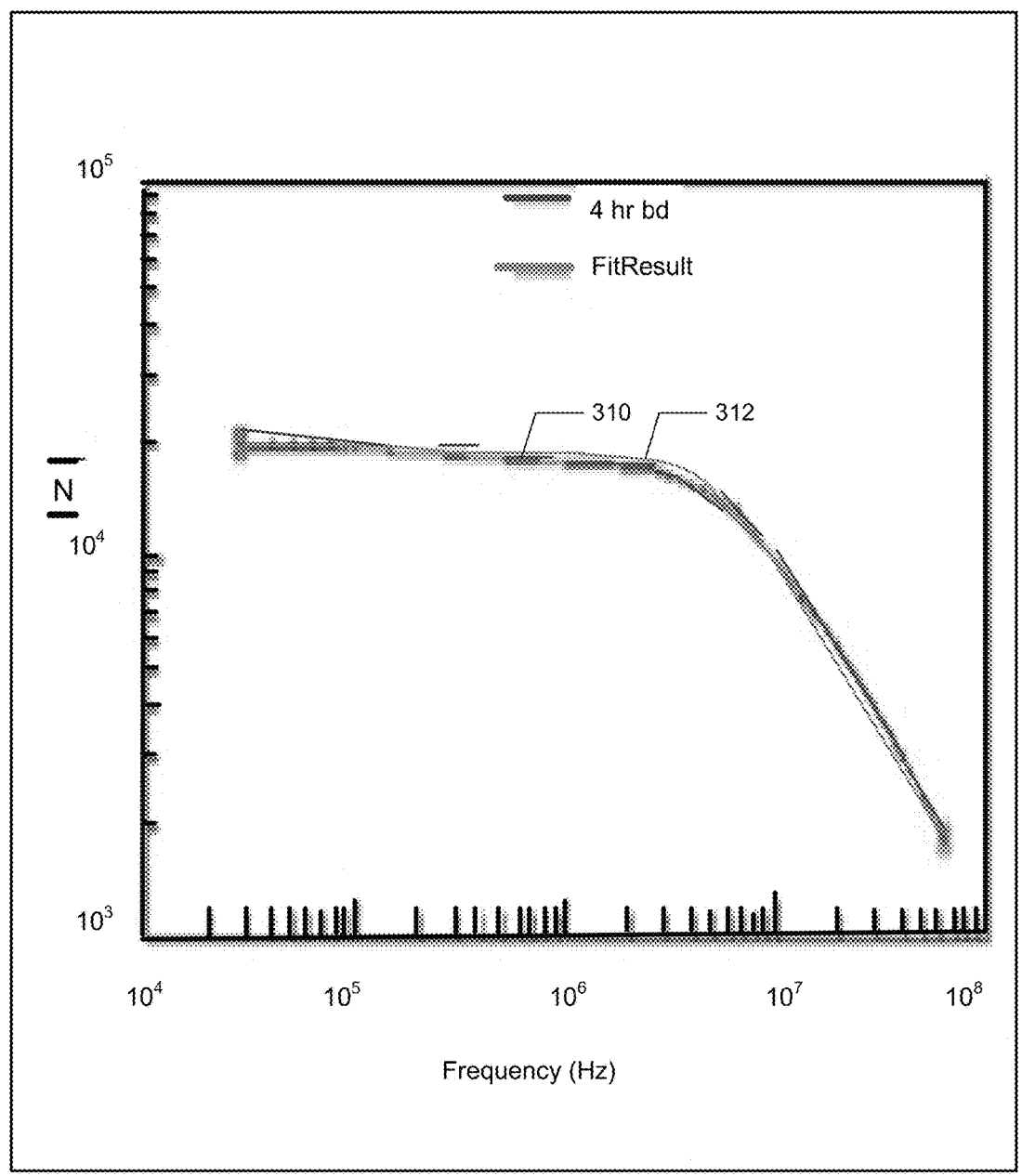
FIGS. 3C and 3D are plots of the same data shown in FIG. 3B plotted as magnitude of impedance (|Z|) (3C) and phase angle (θ) (3D) as functions of frequency.
Figure 3D:
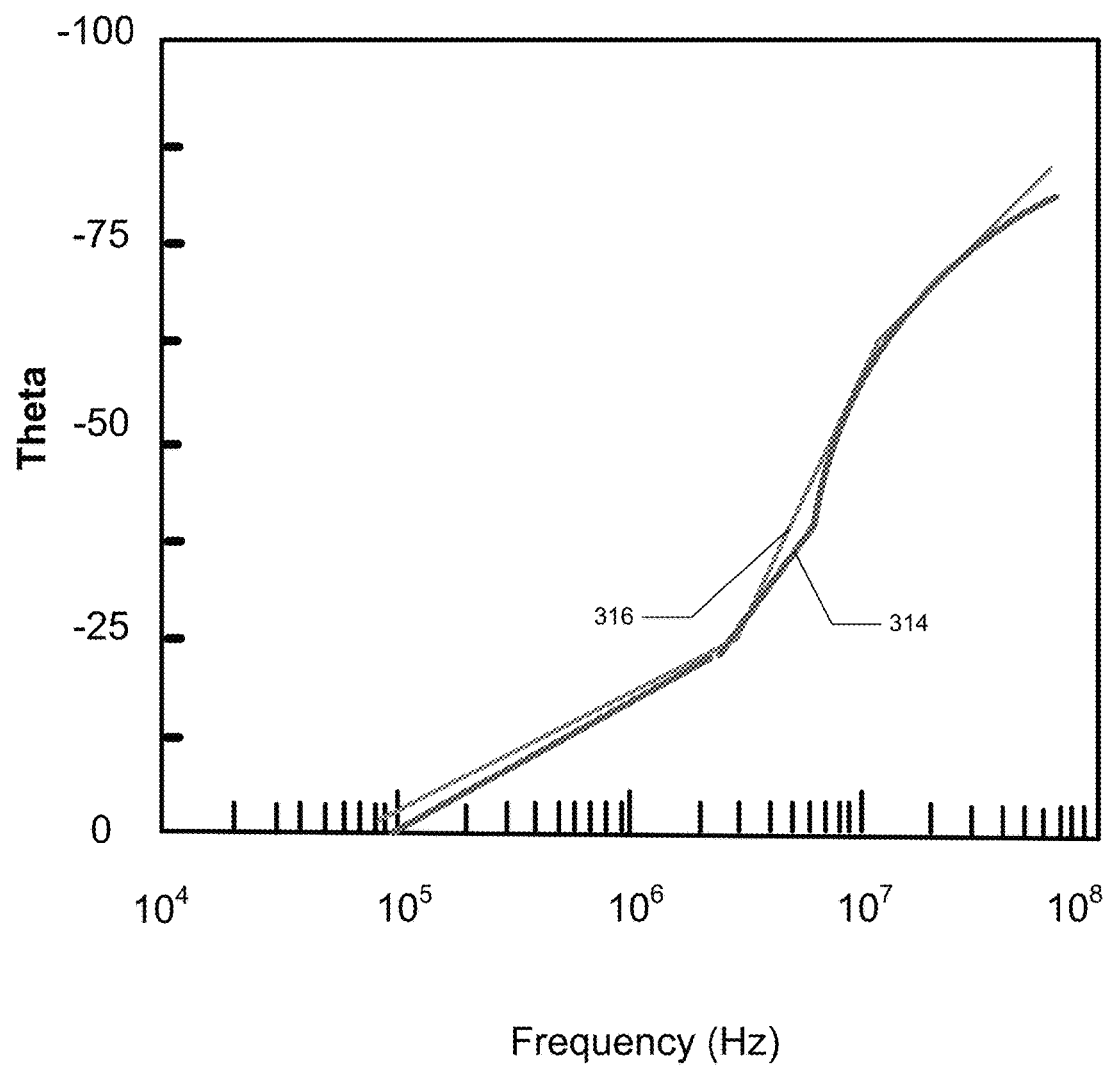

FIG. 3B depicts a plots of impedance obtained from Impedance Analyzer (see analyzer plot 306) as compared to another plot of impedance obtain from fitting via the circuit model with the parameters on the right (see model circuit plot 308). FIG. 3C depicts a plots of the impedance magnitude obtained from Impedance Analyzer (see analyzer plot 310) as compared to another plot of impedance magnitude obtain from fitting via the circuit model with the parameters on the right (see model circuit plot 312). FIG. 3D depicts a plots of the impedance phase obtained from Impedance Analyzer (see analyzer plot 314) as compared to another plot of impedance phase obtain from fitting via the circuit model with the parameters on the right (see model circuit plot 316).

Referring back to FIG. 1B, the parameter calculation module 156 loads a particular impedance data set and the model circuit to which it is fit is constructed. The parameter calculation module 156 then estimates an initial value each of the circuit parameters ($R_e$, $C_e$, $R_b$, CPE-T, and CPE-P) and numerically optimizes the parameter values to obtain the best fit for the system as a whole over the range of frequencies examined. The CPE value determined by the parameter calculation module 156 provides a measure of the charge-storing capability of the suspension being investigated. Over a period of time, this quantity is expected to increase with increase in the number of bacteria, and one can conclusively state that there are viable bacteria in the sample when one observes this quantity (CPE-T) to increase significantly.

According to another aspect, the parameter calculation module 156 determines a corresponding confidence interval for the CPE-T value. A "significant" change is said to occur when a confidence interval of the newer value (as specified by the software fitting the impedance v/s frequency data to the proposed theoretical circuit model of our system) does not overlap with the reference value (usually the zero-hour value). The confidence interval refers to, for example, a range or expected variance of the calculated CPE-T value based on fitting the impedance v/s frequency data to the proposed theoretical circuit model. For example, the initial confidence interval for a calculated CPE-T value of a sample may be 35+/−3 at a first point in time (e.g., 0 hour point) 39+/−2 at second point in time (e.g., 1 hour later), and 45+/−3 at a third point in time (e.g., 2 hours later). In this instance, because the CPE-T value can be as high as 38 at a first point in time and as low as 37 at the second point in time, no "significant" change deemed to have occurred between the 0 hour point and the 1 hour point because the CPE-T values overlap As a result, no viable bacterial is deemed to be present at the 1 hour point. However, because the CPE-T value can only be as low as 42 at the third point in time, a "significant" change is deemed to have occurred between the 0 hour point and the 2 hour point because the CPE-T values do not overlap and, thus, viable bacterial is deemed to be present.

Figure 4:
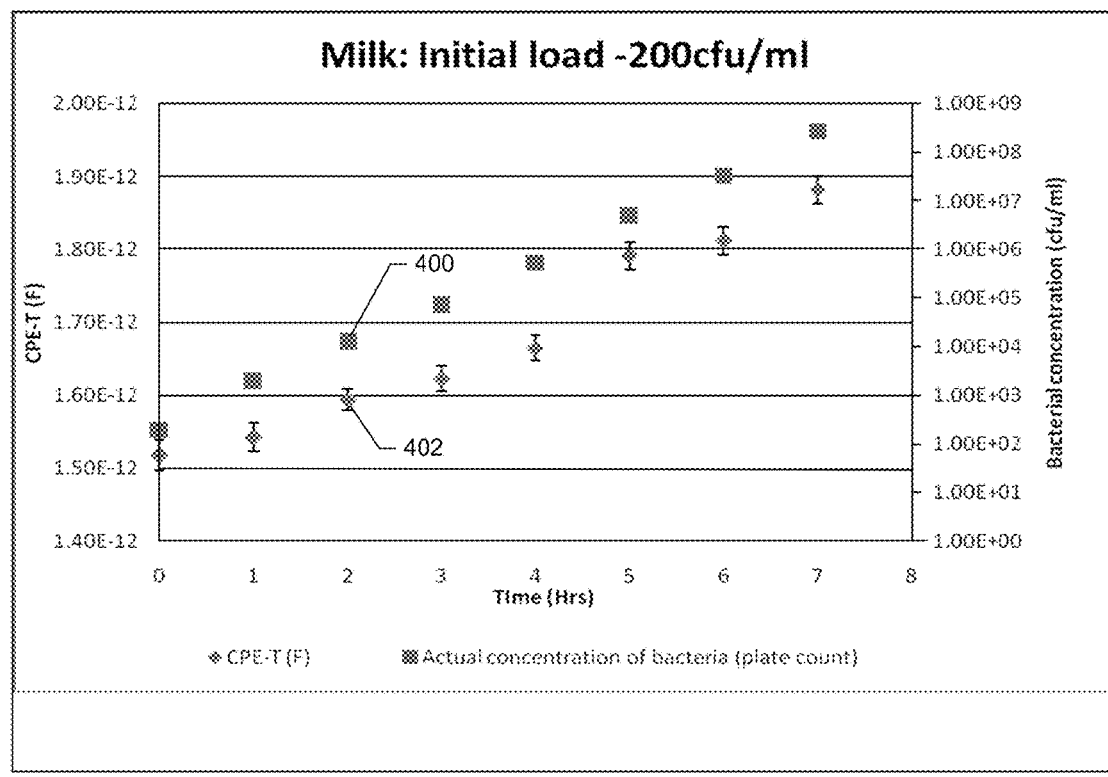
FIG. 4 is a plot showing the increase in a calculated CPE-T parameter calculated by along with actual increase in the concentration of the bacteria in the suspension.

For instance, with reference now to FIG. 4, the reading taken at 1-hour is not significantly different from the initial (0-hour) value because there is overlap between a confidence interval of the CPE-T reading at the zero (0)-hour point and the one (1)-hour point. However, the CPE-T reading taken at the 2-hour point is significantly different because there is no overlap between CPE-T values at the zero (0)-hour point and the two (2)-hour point. The time needed to make this observation (significant increase in the value of CPE-T) is the Time to Detection (TTD) for the present system. For the example depicted in FIG. 4, the TTD is 2 hours). Thus, the pre-determined time interval data may correspond to minimum time required to observe a significant increase in the value of CPE-T for various types of fluid samples.

According to another aspect, the parameter calculation module 156 retrieves the pre-determined time interval data from the data source 122 for the sample being analyzed. As discussed above, the pre-determined time interval data may correspond to the expected Times to Detection (TTDs) of bacteria for individual samples. After the expiration of a time interval defined by the pre-determined time interval data, the parameter calculation module 156 sends a notification to a display of the user interface 103 to notify the user to transfer another portion of the sample to the microfluidic unit 102 for analysis. After transferring another portion of the sample to the microfluidic unit 102, the user connects the microfluidic unit 102 to the VBDS 104 and generates another analysis request 119.

It is contemplated that in other aspects, the parameter calculation module 156 automatically initiates the collections of another portion of the sample being analyzed without the intervention of a user. For example, rather than transferring the notification to the display, the parameter calculation module 156 transfers a transfer notification to a transfer mechanism (not shown) that is configure to collect the other portion of sample. The transfer mechanism may be further configured to connect the microfluidic unit 102 to the VBDS 104 and to generate another analysis request 119.

The data collection module 154 activates the signal generator to generate another series of analysis signals to apply to a different portion of the sample at various frequencies in response to the other analysis request 119 received from the user interface 103. The data collection module 154 also activates the signal analyzer 118 to measure new impedance data of the sample based on the in response to the other analysis request 119. The parameter calculation module 156 then calculates new parametric values of the model circuit based on the new impedance measurement data sets received from the parameter calculation module 156.

The analysis module 158 compares the confidence interval of the at least one of the new impedance parametric values and the confidence interval of the at least one previously calculated impedance parametric values If the two confidence intervals do not overlap, then the analysis module 158 determines that viable bacterial is present.

According to another aspect, if the analysis module 158 determines that the confidence intervals overlap, then the analysis module 158 waits for the pre-determined interval to receive another set of new parametric values of the model circuit from the parameter calculation module 156. This may be an iterative process by which the analysis module 158 performs a series of iterations during a particular time period before determining that there is no bacteria present in the sample. For example, the analysis module 158 may continue to wait for the pre-determined interval to receive another set of new parametric values of the model circuit from the parameter calculation module 156 until the maximum processing time has expired.

According to another aspect, if the analysis module 158 compares a new impedance parametric value, such as a new confidence interval associate with a new CPE-T value with a previously determined confidence interval associate with a previously calculated CPE-T value to see if the values overlap. As discussed above when the new confidence interval value and the previous confidence interval overlap, no viable bacterial is deemed to be present. However, when the new confidence interval value and the previous confidence do not interval overlap, viable bacterial is deemed to be present An output module 160 generates an analysis result for display. According to one aspect, the displayed result indicates whether or not there is viable bacterial present in the sample. According to one aspect, the displayed result may also indicate an amount and/or a type of bacteria present in the sample.

Viable Bacteria Detection Method

Figure 1C:
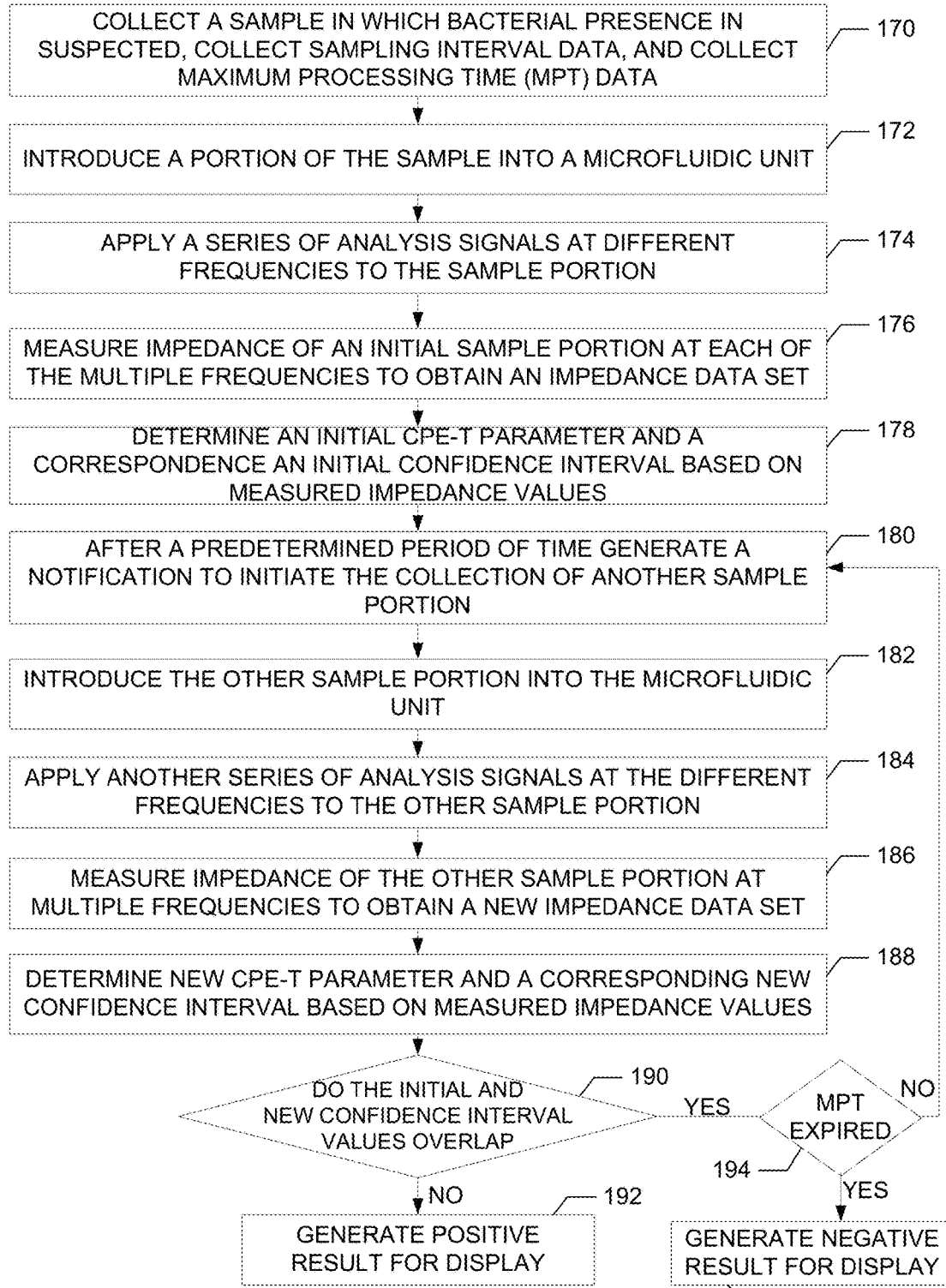
FIG. 1C illustrates a method for detecting viable bacteria in fluid sample in accordance with an aspect of the viable bacteria detection system.

FIG. 1C illustrates a method for detecting the presence of viable bacteria in a fluid sample. At 170, a sample of a fluid sample in which bacterial presence is suspected is collected from a source. An initial portion of the sample is transferred to a microfluidic unit 106 at 172. At 174, a series of analysis signals at different frequencies are generated at the VBDS 104 and applied to the microfluidic unit 106 in response to user input received at the VBDS 104. The VBDS 104 determines an impedance data set by measuring the resulting impedance of the first portion of the sample for each of the analysis signals at 176. At 178, VBDS 104 determines an initial CPE-T value of the model circuit based on the impedance measurements and an initial confidence interval. The VBDS 104 retrieves pre-determined time interval data from the data source 122 for the sample being analyzed and after the expiration of a time interval defined by the pre-determined time interval data, the VBDS 104 sends a notification to a display of the VBDS 104 to notify a user to analyze another portion of the sample at 180.

The other portion of the sample is transferred to the microfluidic unit 106 after the expiration of a time interval at 182. At 184, another series of analysis signals at the same different frequencies are generated at the VBDS 104 and applied to the microfluidic unit 106 in response to another user input received at the VBDS 104. The VBDS 104 determines a new impedance data set by measuring the resulting impedance of the second portion of the sample for each of the analysis signals at 186. At 188, the VBDS 104 determines a new CPE-T value, of the model circuit based on the new impedance measurements and determines a new confidence interval. The VBDS 104 compares the initial confidence interval to the new confidence interval factor to determine if the values overlap at 190. If the initial confidence interval and the new confidence interval values do not overlap at 190, the VBDS 104 displays a positive result indicating that viable bacterial is present in the sample at 192. If the initial confidence interval and the new confidence interval values overlap at 190, the VBDS 104 checks to see if a maximum processing time has expired at 194. If maximum processing time has not expired at 194, the VBDS 104 sends a notification to a display of the VBDS 104 to notify the user to analyze another portion of the sample at 180. If maximum processing time has expired at 194, VBDS 104 displays a negative result indicating that viable bacterial is not present in the sample and ends processing at 196.

Figure 5:
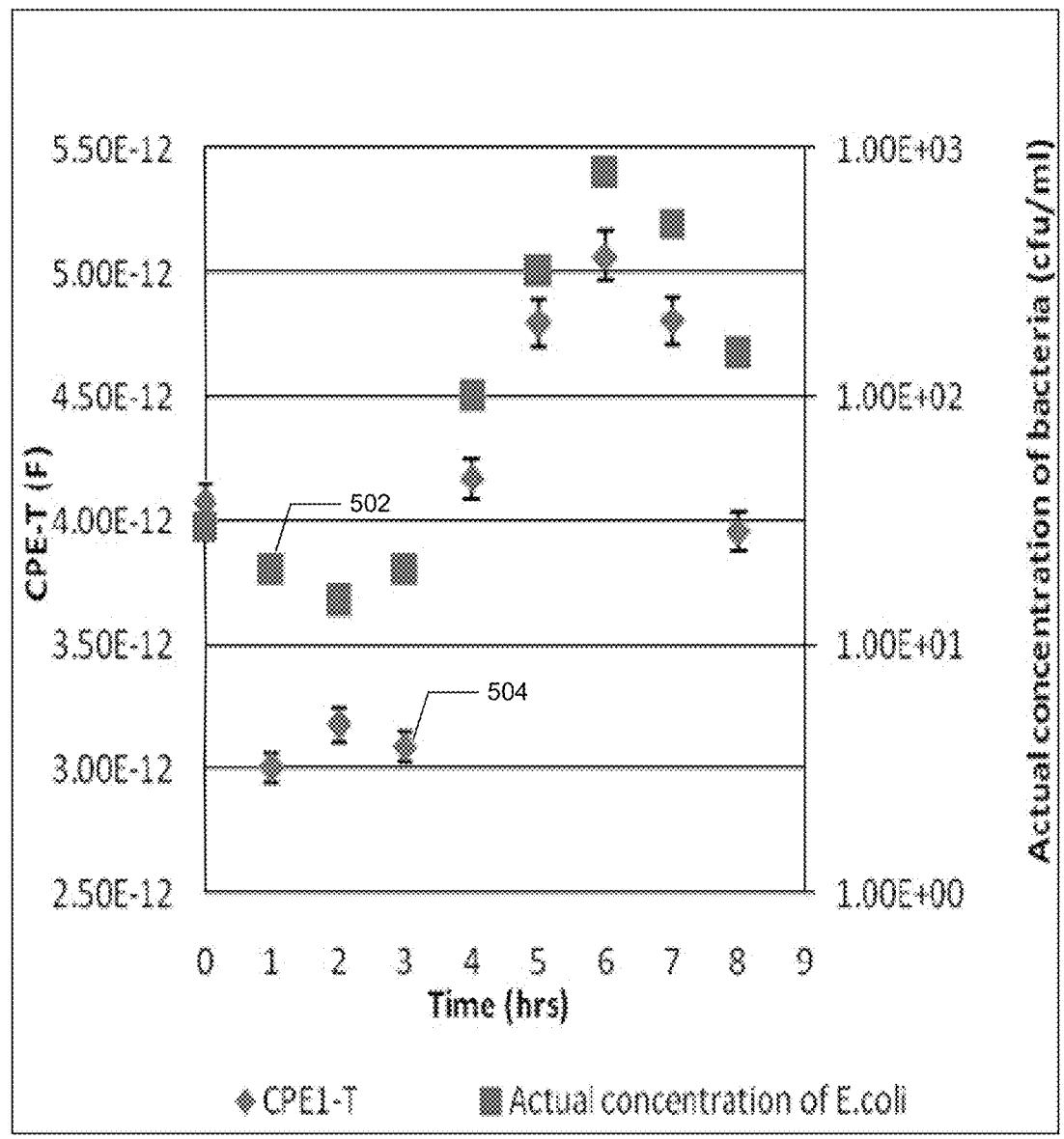
FIG. 5 shows the plot of CPE-T values and actual concentration of bacteria in the sample at various points in time for a system consisting of *E. coli* suspended in Tryptic Soy Broth (TSB).
Figure 6A:
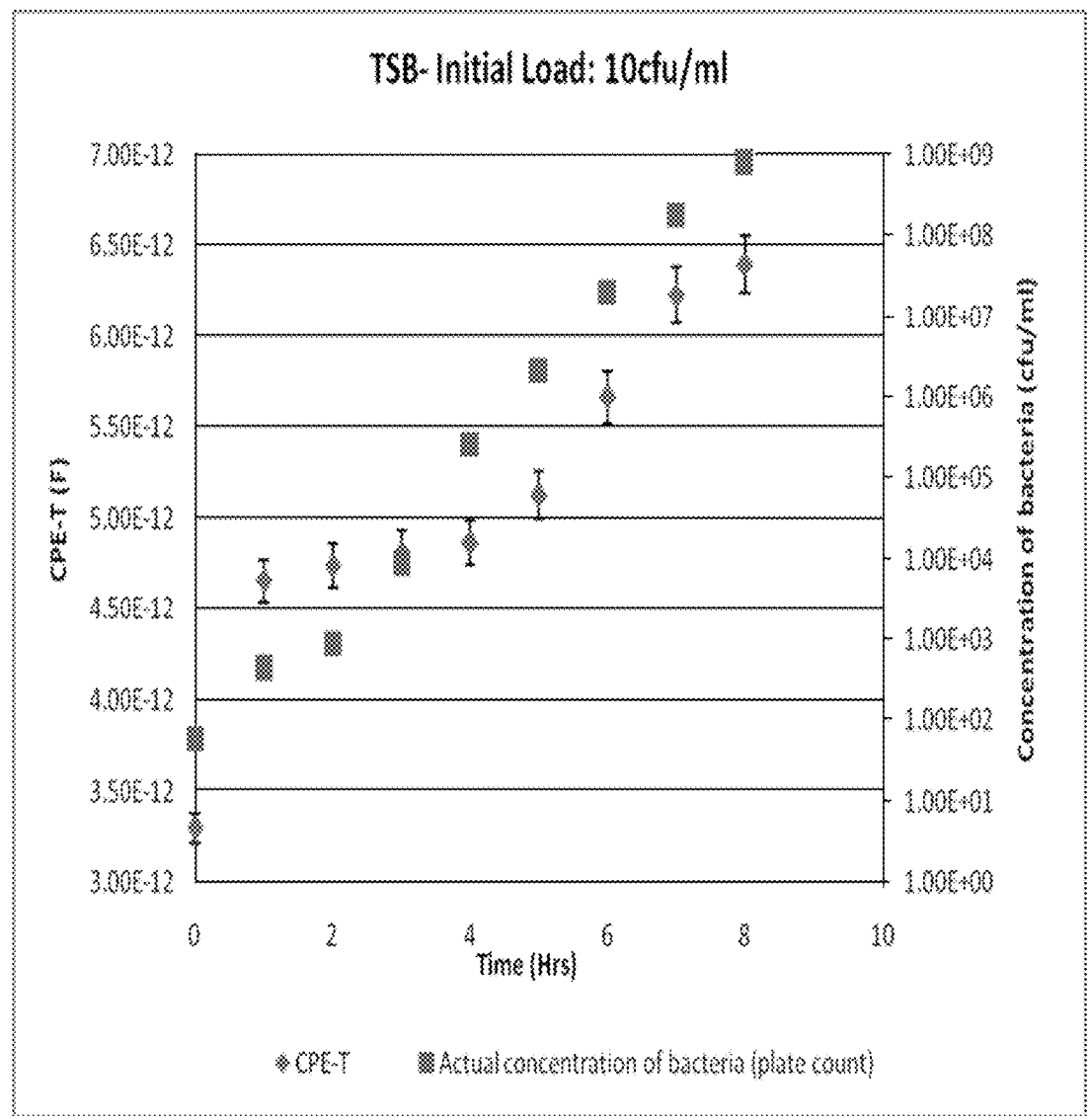
FIGS. 6A-6I are CPE-T v/s time plots for some representative samples with different initial bacterial loads.
Figure 6B:
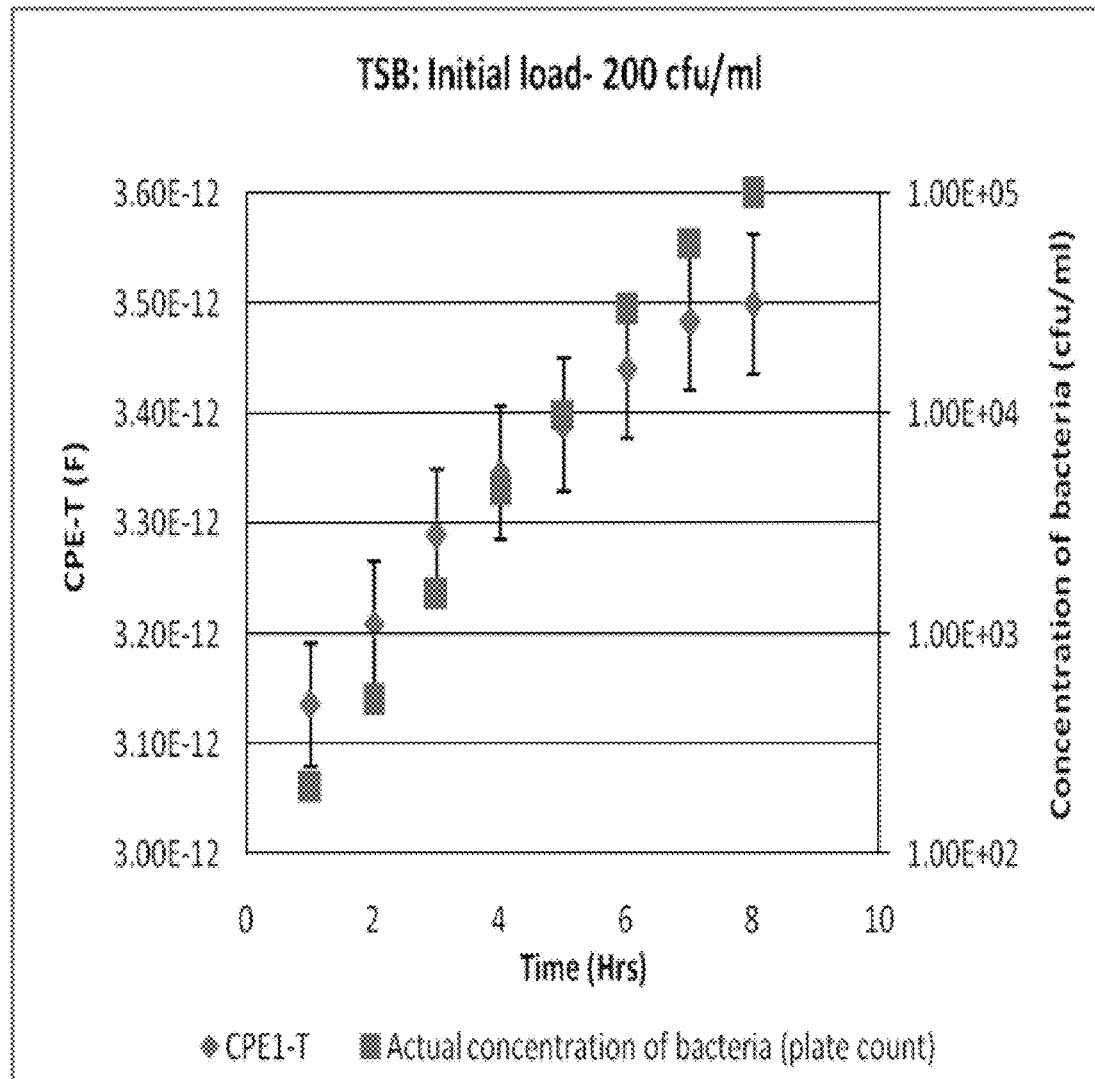
Figure 6C:
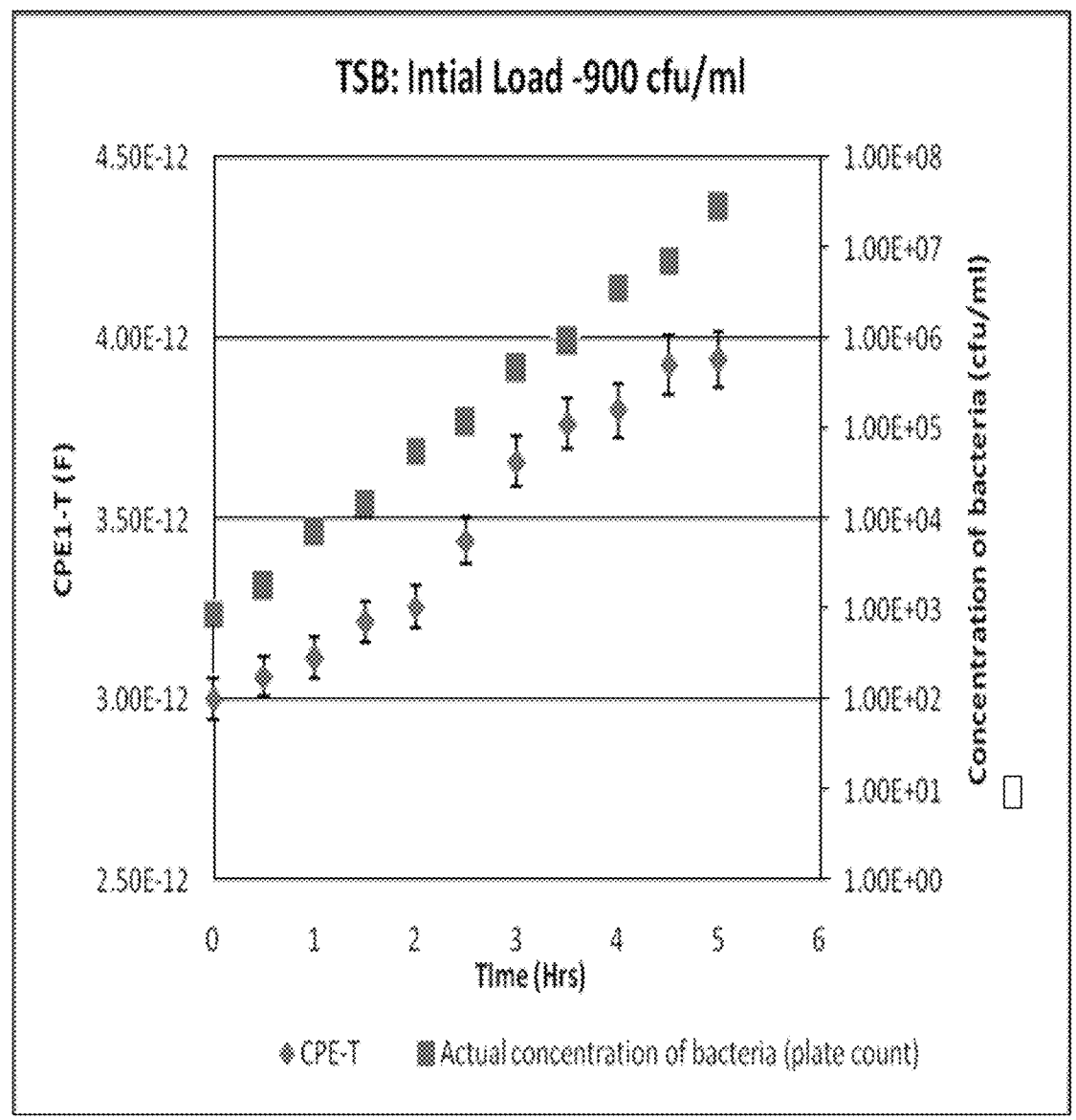
Figure 6D:
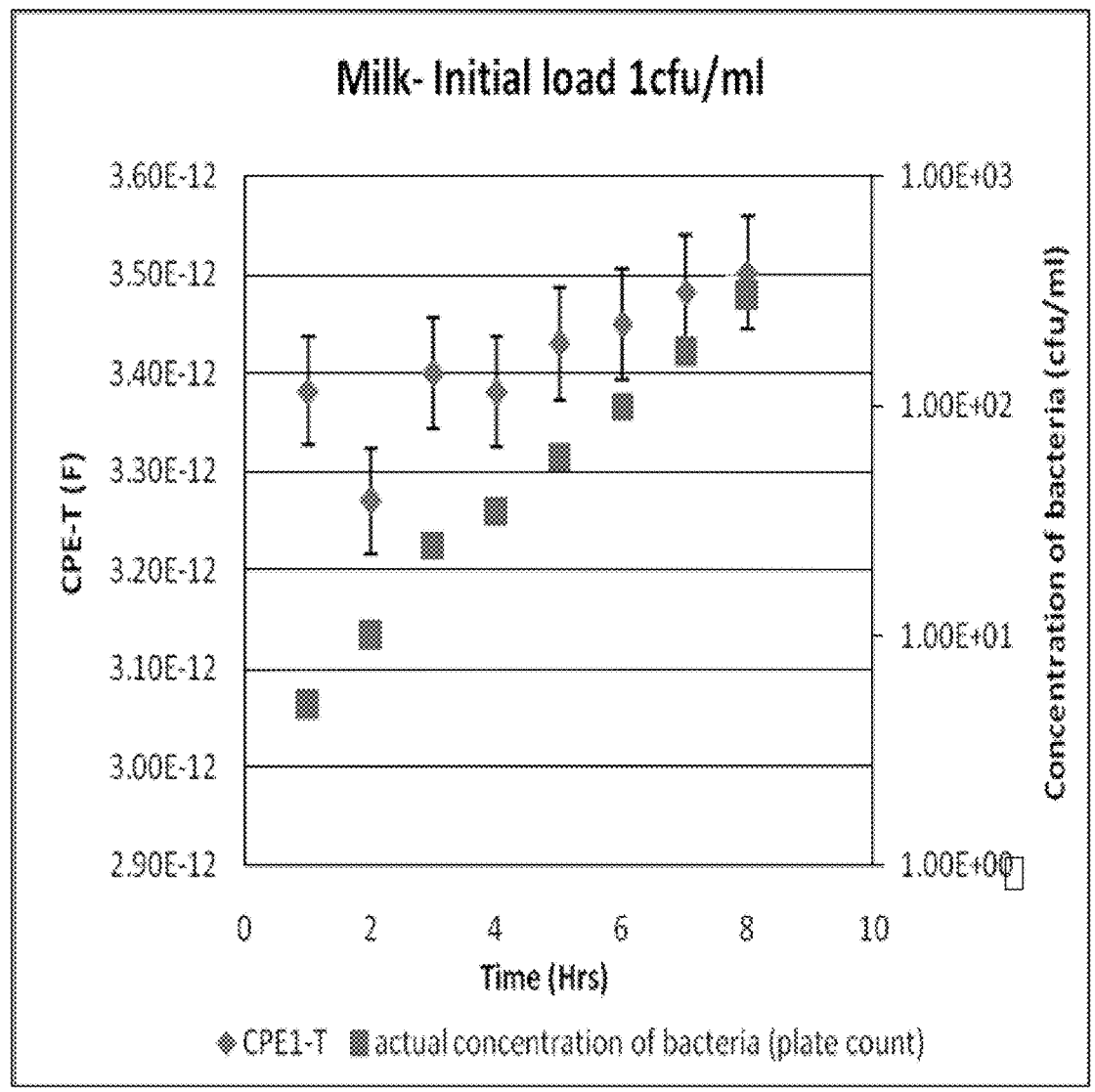
Figure 6E:
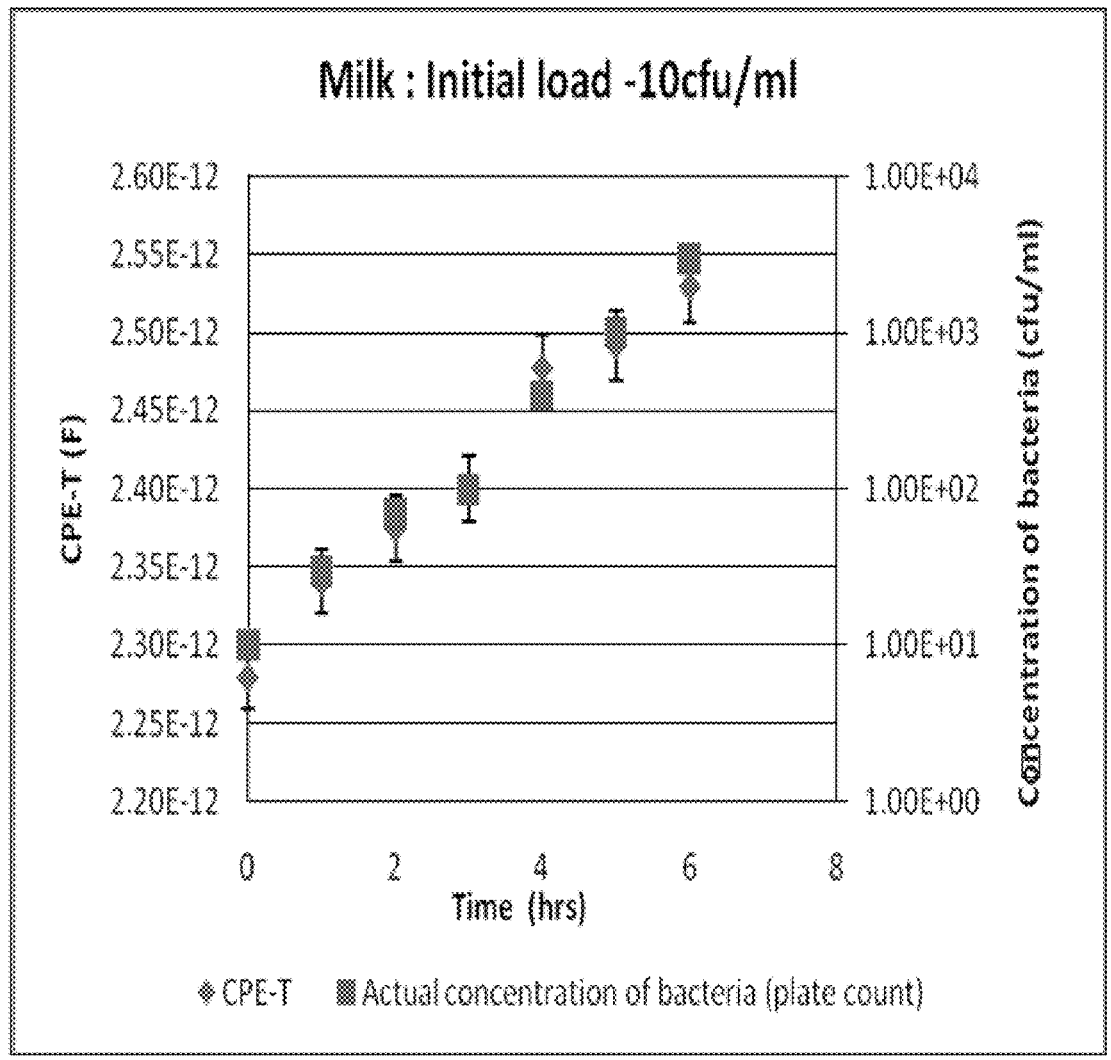
Figure 6F:
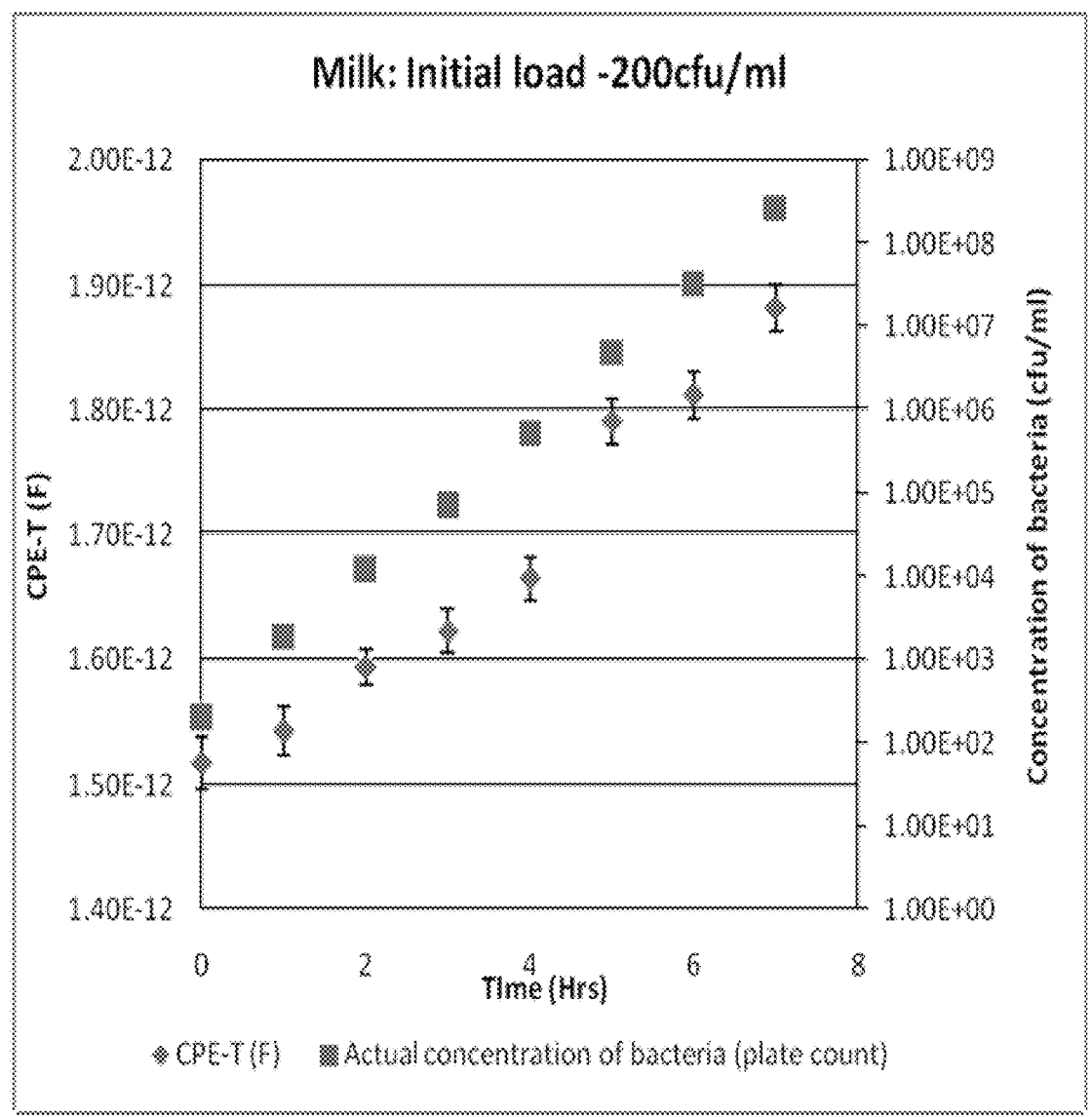
Figure 6G:
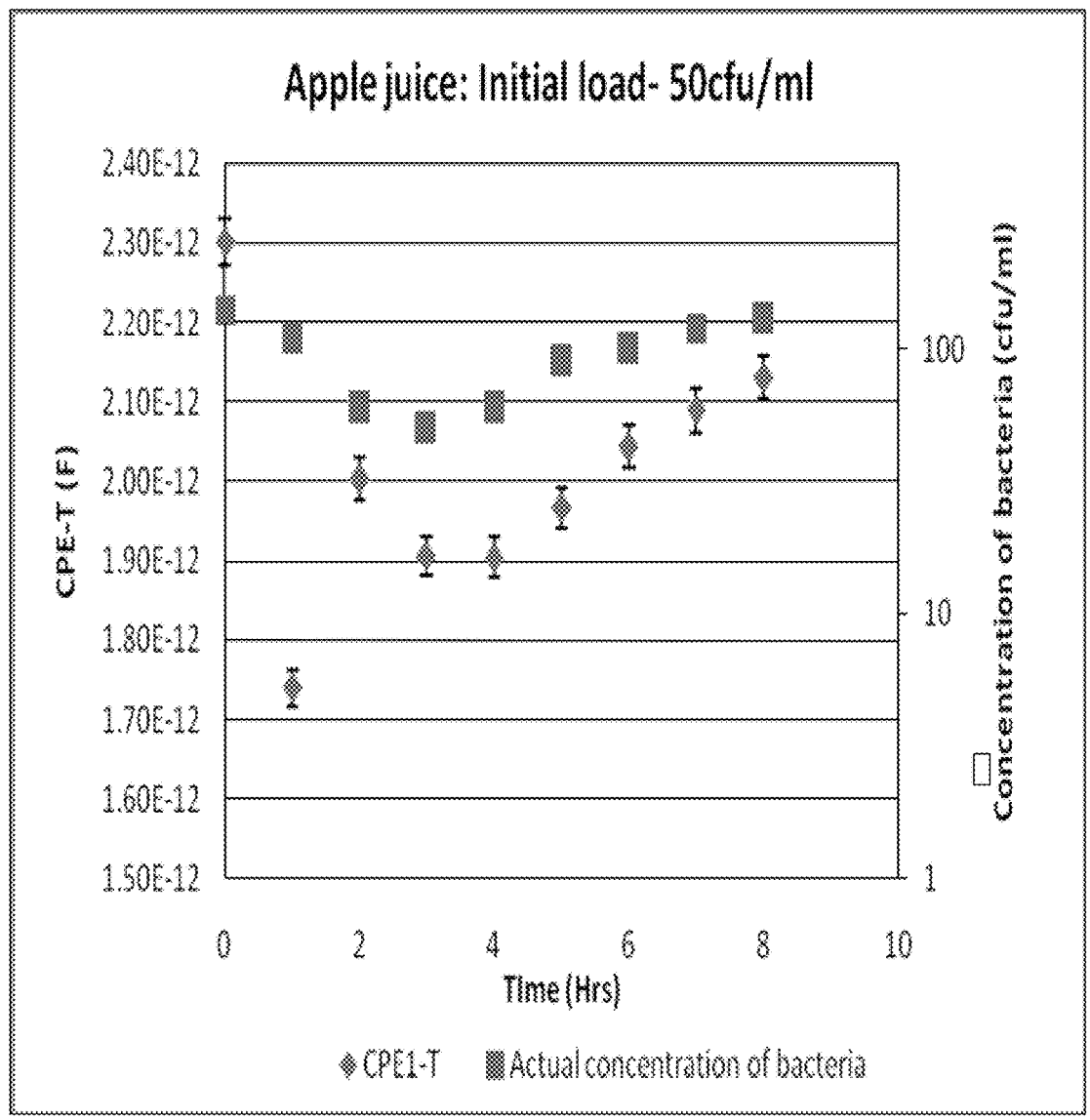
Figure 6H:
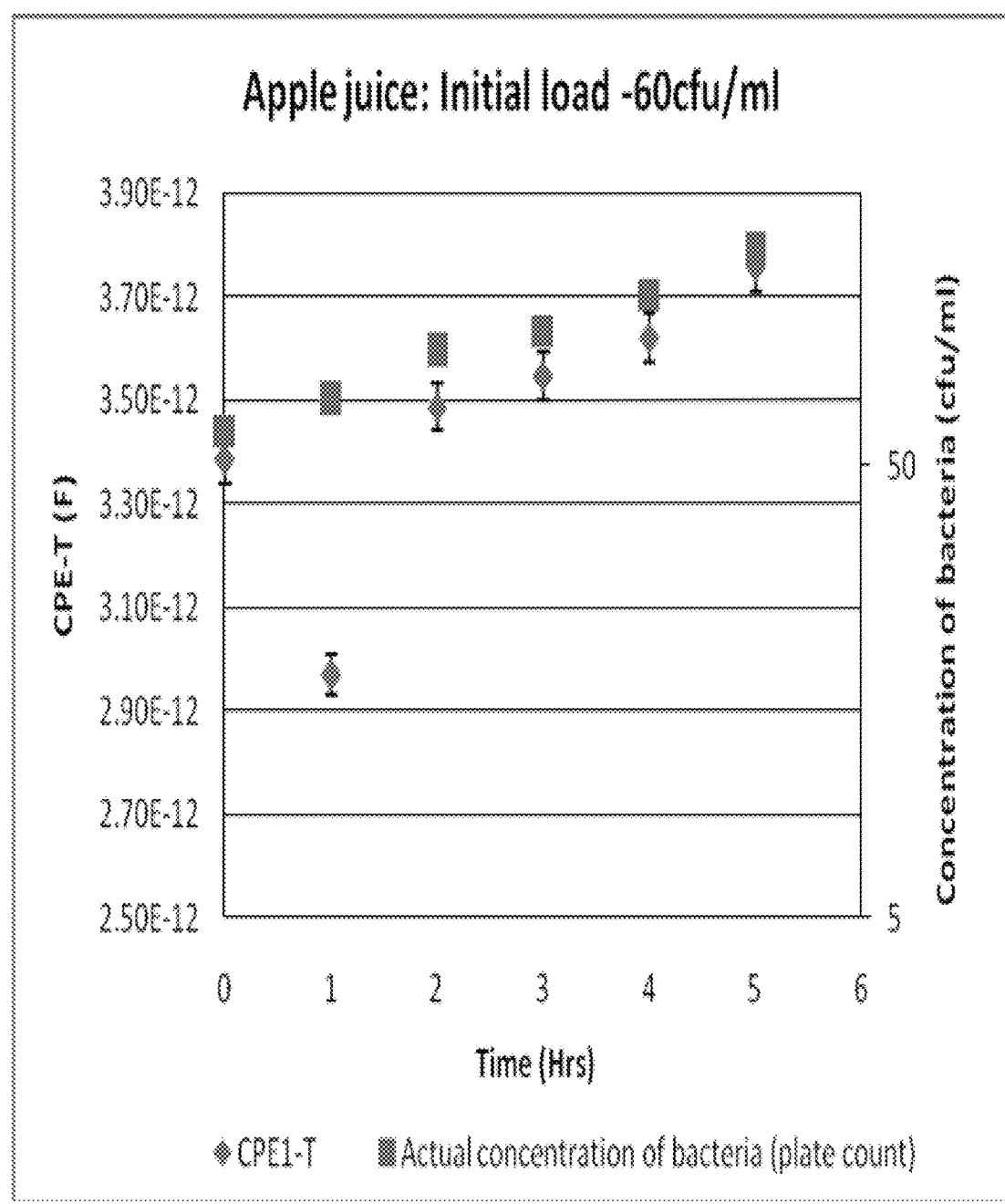
Figure 6I:
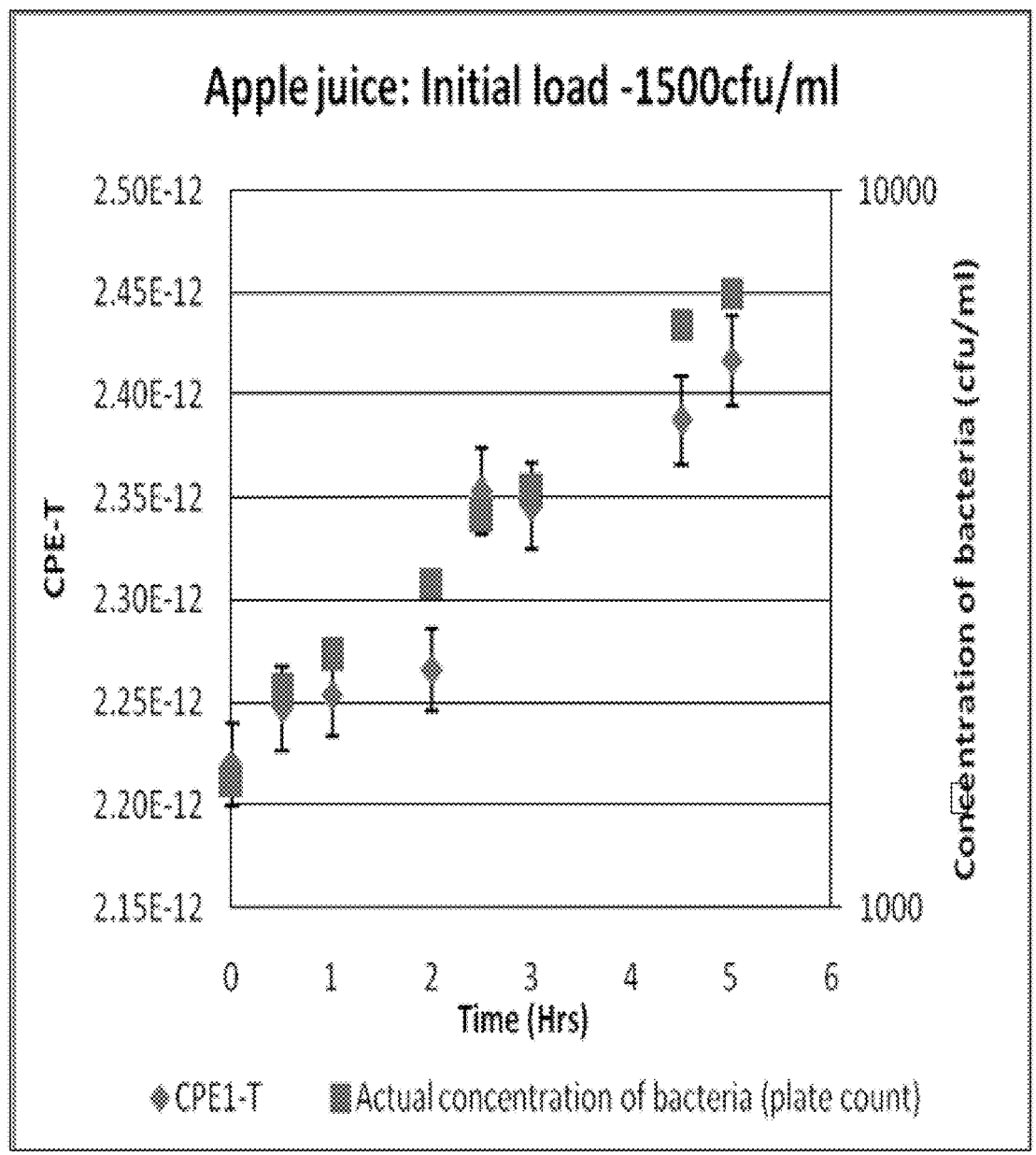

Ability of the calculated CPE-T value to track true bacterial counts: As can be seen in FIG. 5, using the value of CPE-T as an indicator of bacterial load in the system, closely tracks the actual bacterial numbers present (as obtained using plate counts) irrespective of whether the bacterial numbers hold steady (as occurs in the lag and saturation/stationary phase), rise, or decline. The decrease in CPE-T values as bacteria die off seems to indicate that dead bacteria are not as capable as live ones of storing charge.

Example Times to Detection

Times to Detection (TTD) as a function of initial bacterial loads: Three types of samples (TSB, Milk and apple juice) were inoculated with 4 different initial bacterial loads (targeted to be 1, 10, 100, 1000 CFU/ml), impedance measurements were taken at specific intervals (half hour or one hour), and the impedance data were analyzed using Z view software to obtain the CPE-T values as described in the previous section. These values were used to obtain TTDs using the criteria explained using FIG. 4. FIG. 4 is a plot showing the increase in the bulk capacitance (e.g., see diamond 402) with actual increase in the concentration of the bacteria (e.g., see square 400) in the suspension. The plot also indicates the time to detection (shown by the arrow), For this sample, the error bar of CPE-T value of 2 hours does not overlap with the error bar of zero-hour reading and hence 2 hours is considered as the time to detection. Some more of such typical plots of CPE-T vs time which gives the TTDs for each sample are shown in FIGS. 6A-6I, with the arrows indicating the TTD for that sample with respective initial bacterial load.

In a few cases, mostly for *L. acidophilus* in apple juice, a significant lag phase is observed. During this period, the actual concentration of bacteria (e.g., square 502 of FIG. 5) did not grow, and sometimes even die—as indicated by the plate count data. In such cases, a better estimate of the capabilities of the present system is obtained by subtracting the lag phase time (e.g., 2 hours) when calculating the Time to Detection for the given initial load in the given system. For example, in the case shown in FIG. 5, although the significant increase in CPE-T (e.g., diamond 504 of FIG. 5) from the initial value is detected only at the fourth hour, the TTD of the system is taken to be 2 hours since for the first two hours, the bacteria in the suspension were in the lag phase.

Figure 7A:
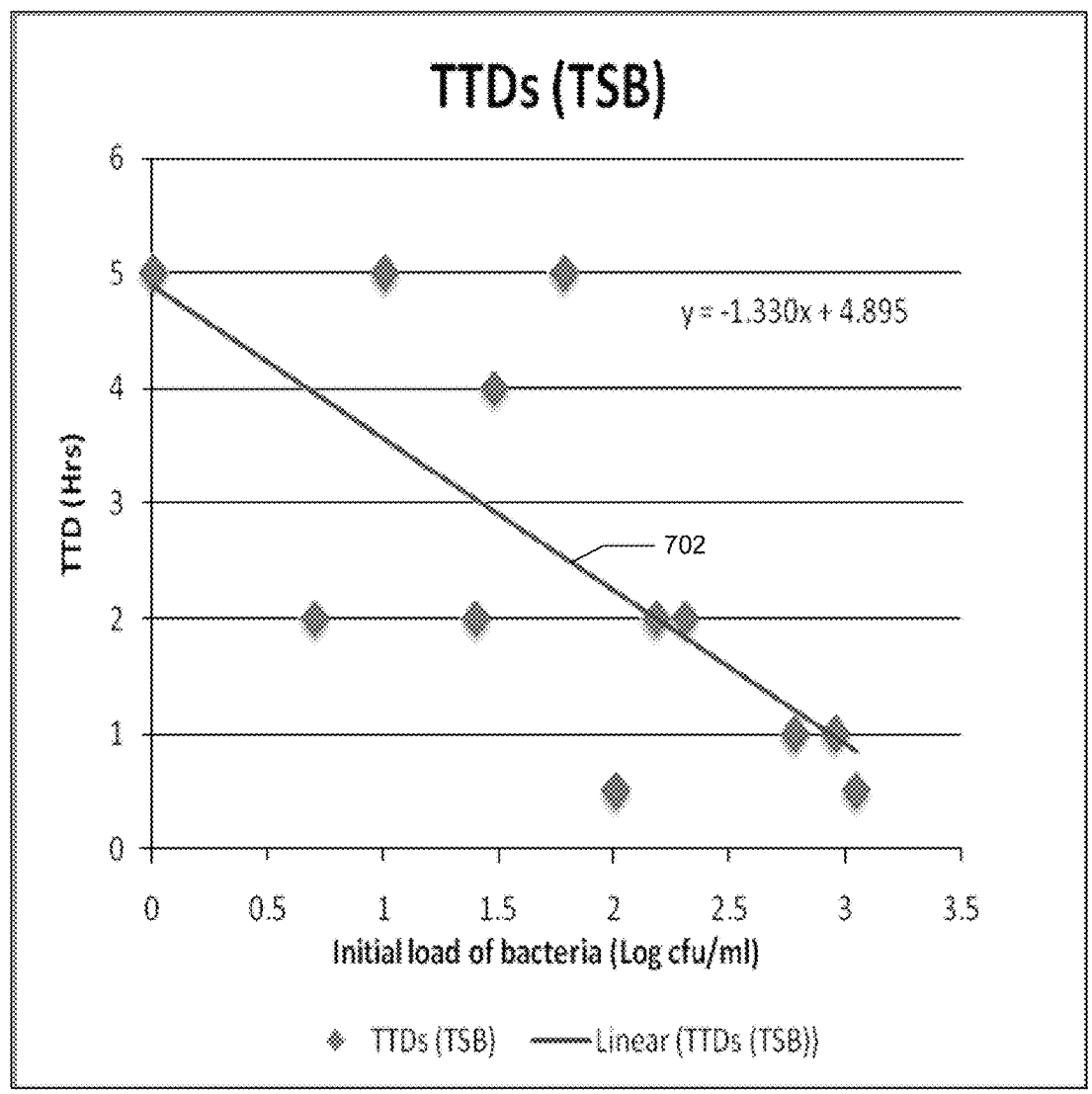
FIGS. 7A-7C are the consolidated plots showing the variation of the Time to Detection (TTD) as a function of the initial bacterial load for multiple experiments with *E. coli* in Tryptic Soy Broth (left), *E. coli* in milk (center), and *Lactobacillus* in apple juice (right)
Figure 7B:
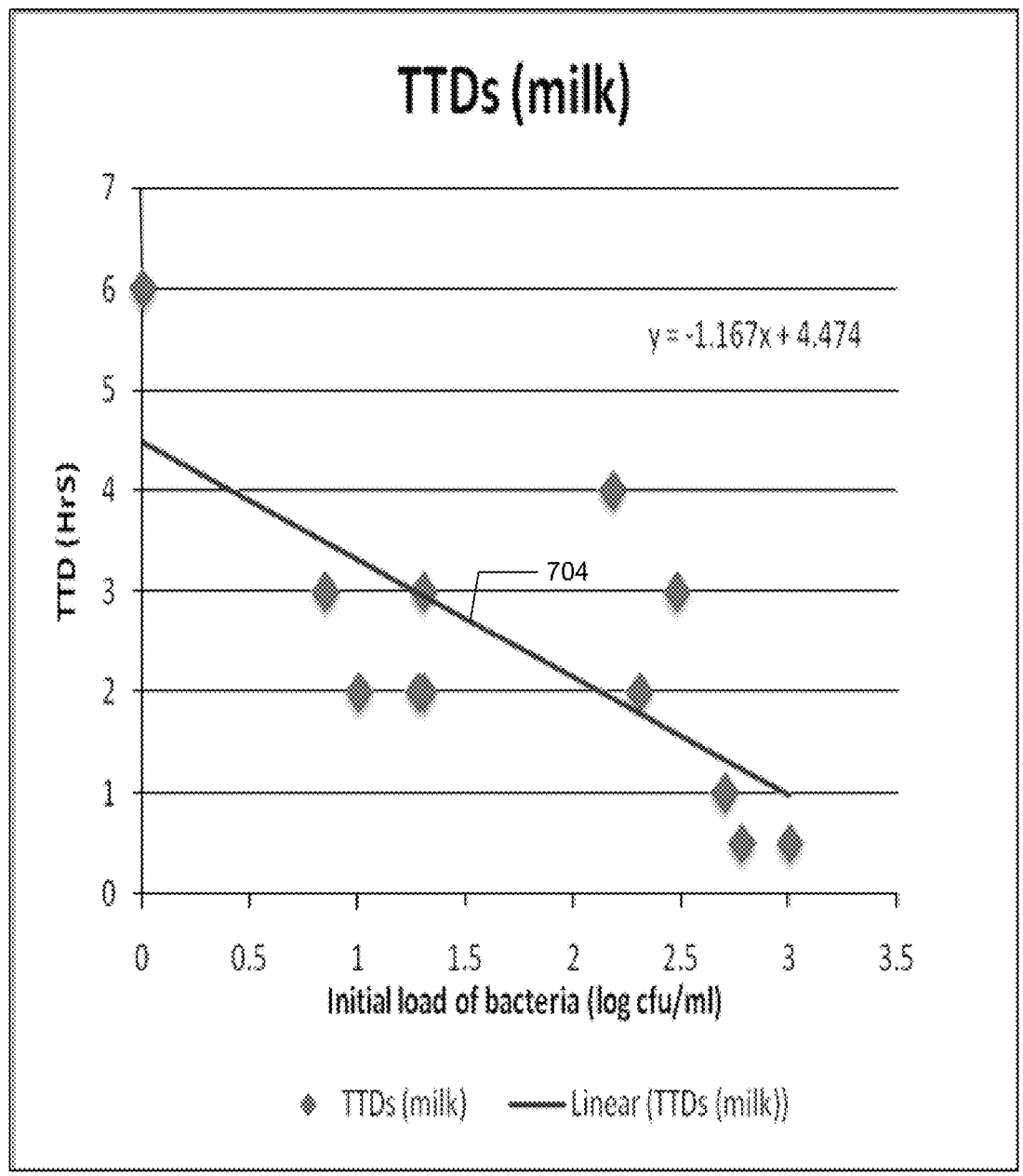
Figure 7C:
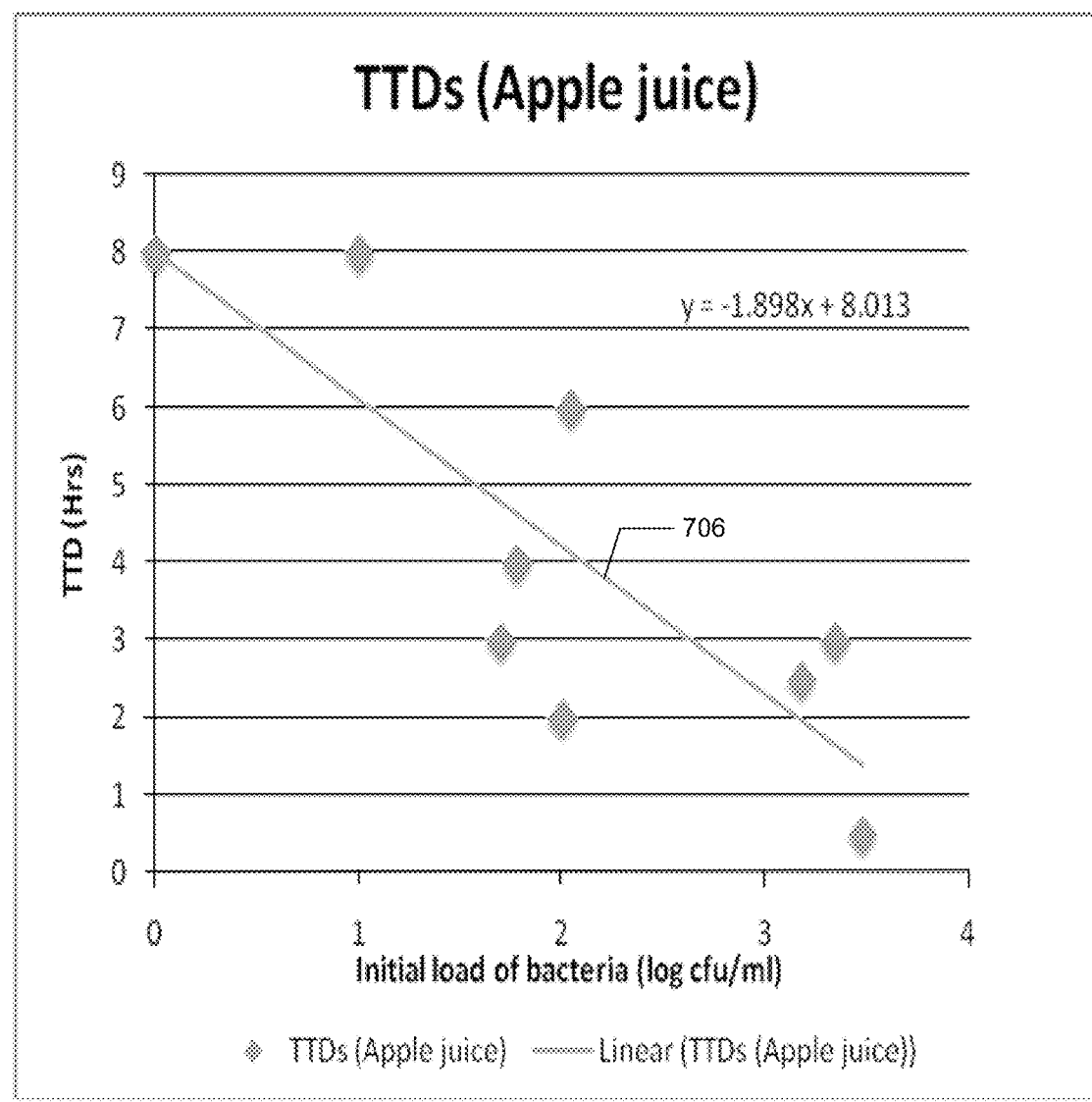

Each experiment with the targeted initial load of bacteria in a specific sample is repeated three times to ascertain the reproducibility of the method. A more accurate estimate of the true value of the initial loads could only be obtained the next day, once plate counts were obtained. Hence, twelve points each have been taken for TSB, milk, and apple juice (some of these points overlap very closely, and are hence not distinguishable). These points are used to calculate a line of bet fit using linear regression, and these lines are also shown in FIGS. 7A-7C. The equations for these lines provide the best estimate of the time that the present system will take to detect a given load of a particular type of bacterium in a particular substrate.

As seen in from the plots 702, 704, 706 shown in FIGS. 7A-7C, respectively, there is an inverse relationship between the (log) initial load of bacteria in a sample, and the TTD of proliferating bacteria using the present system and method. In this it is similar to methods that rely on detecting the effects of bacterial metabolism such as Bactometer, RABIT etc. This is expected since the presence of more bacteria (our method) also leads to increased metabolite consumption/generation. Also, as in the case of RABIT, Bactometer etc., one can generate a calibration plot for a particular type of suspension, and the TTD can be used to estimate the initial load of the system. The scatter observed is qualitatively comparable to the data used to generate calibration curves for RABIT etc. The scatter arises due to multiple reasons. For example, two such reasons include uncertainties in the estimates of the initial loads and differences in metabolic state of members within and between populations seeded. In other words, although the plot of TTDs against a "known" initial load is based on plate counts, this "known" value itself is subject to some degree of uncertainty—typically of the order of the square root of the true number of particles present (Poisson distribution). Thus, if the suspension being incubated had 100 CFU/ml of bacteria (true value), it is expected that a 100 µl sample introduced into a microfluidic unit, or use for plating, will have 10 CFUs. However, there is also a 33% chance that isolated sample will have either less than 7 (10–√10), or greater than 13 (10+√10) bacteria. In addition, a certain fraction of the bacterial cells that constitute the inoculum may remain in the lag phase slightly longer than others. This may not be readily captured by the plate counts taken to determine initial load (since in plates, they get adequate time to grow). When operating at low concentrations (low numbers of bioparticles), such sampling uncertainties have the potential to introduce a greater relative error. However, despite these sources of error, the TTD data still shows a clear trend in the manner expected (inverse with respect to log initial load).

Another characteristic of the present method is that the TTD is a function of the doubling time of the proliferating bacteria. The faster that a given bacterium doubles, the shorter is TTD in the present invention. For example, *E. coli* K-12 bacteria that have a doubling time of 27 minutes at 37° C., and *Lactobacillus acidophilus* has a doubling time of 50-60 minutes at 30° C. Thus the doubling time of *lactobacillus* is about 2 times that of *E. coli*. The TTDs for *lactobacillus* are also correspondingly longer (8 hours for 1 CFU/ml and 4.5 hours at 100 CFU/ml v/s 4.5 hours and 2 hours, respectively, for E. coif at the same initial loads). For initial loads of 1000 CFU/ml or higher, proliferation was detected in half an hour (the shortest time interval used) for *E. coli* (and in one case, for *lactobacillus* as well). Thus, at these relatively higher loads, bacteria can be detected within one cycle of division. For lower initial bacterial loads, at the points in time where significant changes in CPE-T values are detected, their concentration in the sample (as estimated from the plate counts) is typically between 200-1000 CFU/ml. As a rough ballpark estimate, the present invention detect bacteria in the act of doubling their numbers when there are about 500 of them present per ml of suspension.

Figure 8A:
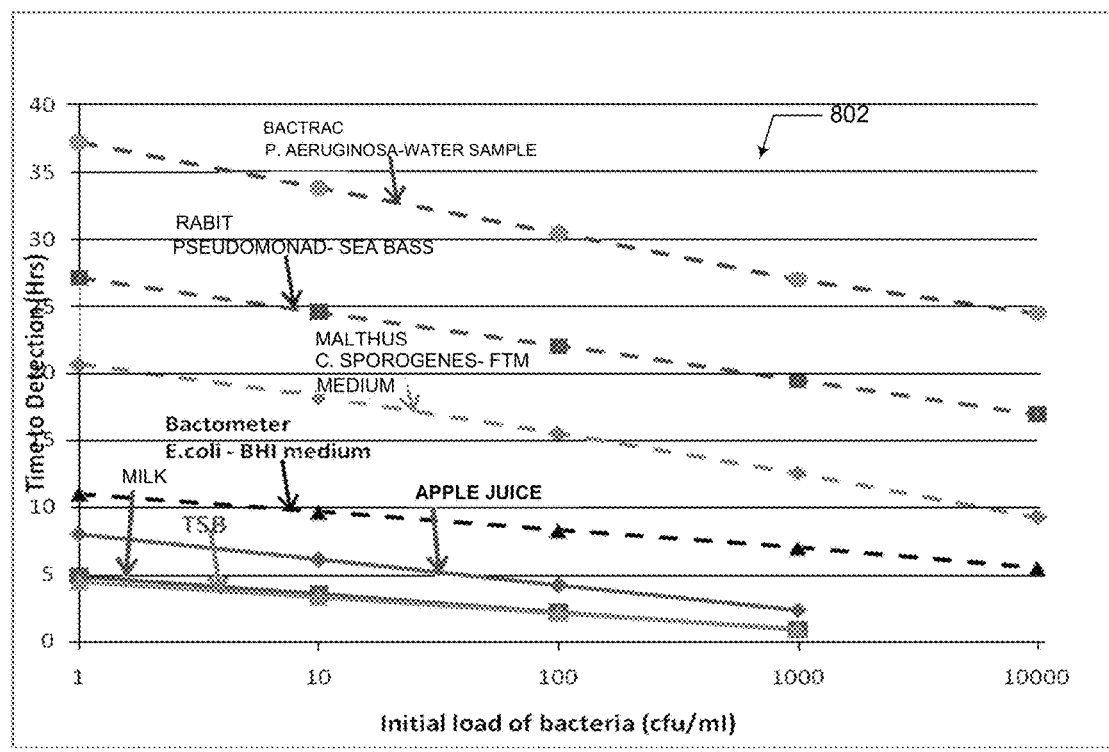
FIGS. 8A and 8B compares TTDs obtained using the present invention (solid lines) to (A) those of the commercial systems already on the market, and (B) other, especially microfluidic, systems under development (dashed lines).
Figure 8B:
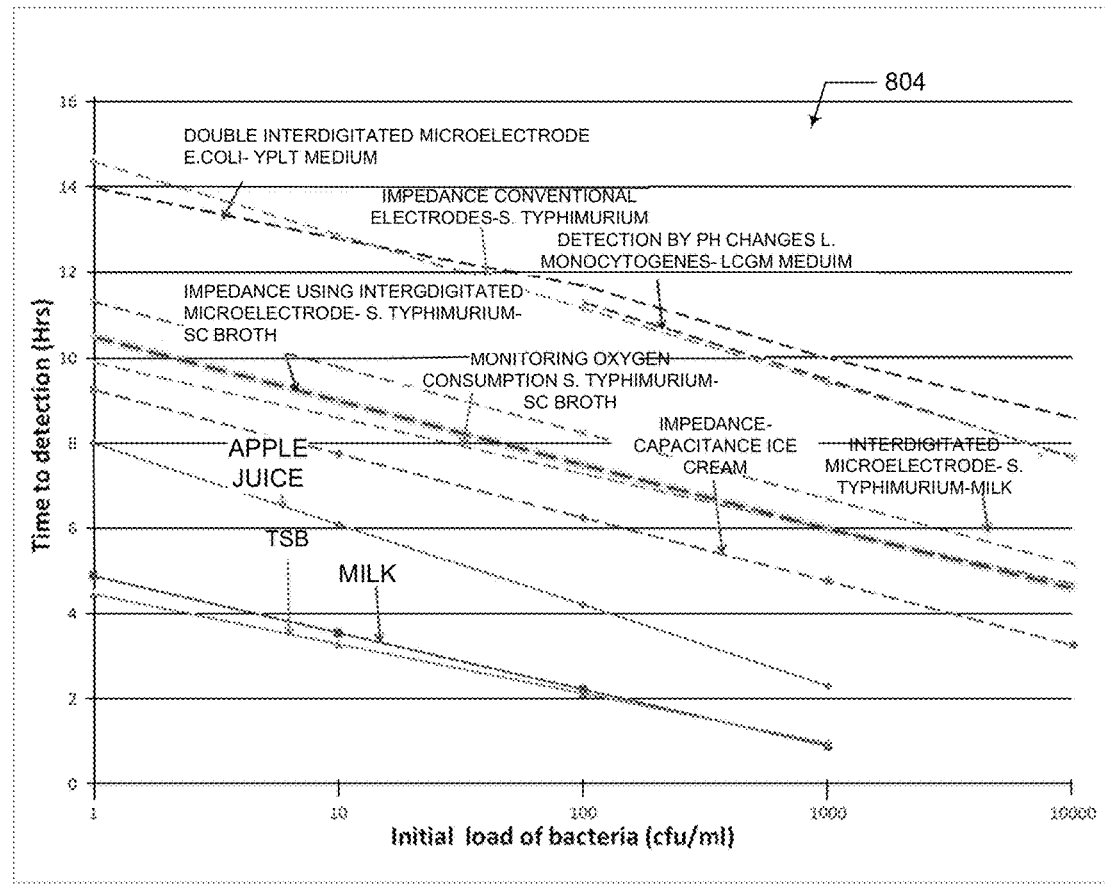

As shown in FIGS. 8(*a*) and 8(*b*), the TTDs of the present invention compare very well with automated techniques already on the market and other automated techniques in development. FIG. 8(*a*) is a graph 802 that provides the comparison of the present detection method with that of previously available commercial automated systems, such as RABIT™, Malthus 2000™, Bactometer™, and BacTrac™. FIG. 8(*b*) is a graph 804 that provides the comparison between the present system and some of the systems currently under development. Virtually all of these systems under development continue to rely on detecting the effects of bacterial metabolism on the medium properties, such as changes in pH, Conductivity, oxygen concentration, for detection. Some employ features and capabilities available through microfluidic systems, such as micro-interdigitated electrodes or pre-concentration using dielectrophoresis to try and reduce the overall TTDs. While they achieve low TTDs (3-9 hrs) for very high initial concentrations of bacteria (~10,000 CFU/ml), they continue to have high TTDs (10-14 hours) at low initial concentration of bacteria (1 CFU/ml). Thus, for any given initial load, the inventive system is able to detect bacteria at least 3 to 4 times faster than other methods.

What is claimed is:

1. A system to detect viable organisms in a fluid sample, the system comprising:
    a sample collection system containing a growth medium to receive the fluid sample;
    a channel to receive a portion of the fluid sample from the collection system; and
    a detection system in communication with the channel to measure a bulk capacitance of the portion of the fluid sample received in the channel, where the bulk capacitance corresponds to a concentration of the viable organisms within the fluid sample; wherein the detection system generates a plurality of analysis frequencies from 1 kHz up to and including 100 Mhz.

2. The system of claim 1, where the organism is a pathogen.

3. The system of claim 1, where the detection system is further configured to determine a baseline bulk capacitance for the portion of the fluid sample and determine a change in the bulk capacitance over time, where the change in the bulk capacitance indicates an increase in the concentration of organisms in the fluid sample.

4. The system of claim 1, where the detection system is further configured to determine a baseline bulk capacitance for the portion of the fluid sample and determine a change in the bulk capacitance over time, where the change in the bulk capacitance indicates a decrease in the concentration of organisms in the fluid sample.

5. The system of claim 1, where the detection system is further configured to determine a baseline bulk capacitance for the portion of the fluid sample, where the baseline bulk capacitance indicates the absence of an organism in the fluid sample.

6. The system of claim 1, where the portion of the fluid sample received in the channel also includes conductive and capacitive elements defining an electrode-solution interface capacitance at an interface between the fluid and an electrode of the detection system.

7. The system of claim 1, where the detection system measures the bulk capacitance in the portion of the fluid sample in response to three or more analysis frequencies generated by the detection system.

8. The system of claim 1, where the channel receives another portion of the fluid sample from the collection system and the detection system determines a change in the bulk capacitance between the portion of the fluid sample and the other portion of the fluid sample.

9. The system of claim 8, where the other portion of the fluid is automatically collected after a time interval.

10. The system of claim 9, where the detection system measures the bulk capacitance in the other portion of the fluid sample in response to three or more analysis frequencies generated by the detection system.

11. The system of claim 1, where the detection system comprises a processor to execute an organism detection application.

12. A method to detect viable organisms in a fluid sample, the method comprising:
collecting the fluid sample in a sample collection system containing a growth medium;
transferring a portion of the fluid sample from the collection system to a channel; and
measuring a bulk capacitance of the portion of the fluid sample at a detection system in communication with the channel, where the bulk capacitance corresponds to a concentration of the viable organisms within the fluid sample.

13. The method of claim 12, where the organism is a pathogen.

14. The method of claim 12 further comprising:
determining a baseline bulk capacitance for the portion of the fluid sample;
determining a change in the bulk capacitance over time, where the change in the bulk capacitance indicates at least one of an increase in the concentration of organisms in the fluid sample, a decrease in the concentration of organisms in the fluid sample, or the absence of an organism in the fluid sample.

15. The method of claim 12 further comprising:
determining an electrode-solution interface capacitance at an interface between the fluid and an electrode of the detection system.

16. The method of claim 12 further comprising:
generating three or more analysis frequencies with the detection system; and
measuring the bulk capacitance in the portion of the fluid sample in response to the three or more analysis frequencies.

17. The method of claim 16 further comprising:
transferring another portion of the fluid sample from the collection system to the channel; and
determining a change in the bulk capacitance between the portion of the fluid sample and the other portion of the fluid sample.

18. The method of claim 17 further comprising:
generating the three or more analysis frequencies with the detection system; and
measuring the bulk capacitance in the other portion of the fluid sample in response to the three or more analysis frequencies.

* * * * *